US012644852B2

(12) United States Patent
Kawai et al.

(10) Patent No.: US 12,644,852 B2
(45) Date of Patent: Jun. 2, 2026

(54) HYDROGEN DETECTION DEVICE AND CONTROL METHOD FOR HYDROGEN DETECTION DEVICE

(71) Applicant: Nuvoton Technology Corporation Japan, Kyoto (JP)

(72) Inventors: Ken Kawai, Osaka (JP); Kazunari Homma, Gifu (JP); Koji Katayama, Nara (JP)

(73) Assignee: NUVOTON TECHNOLOGY CORPORATION JAPAN, Kyoto (JP)

( * ) Notice: Subject to any disclaimer, the term of this patent is extended or adjusted under 35 U.S.C. 154(b) by 308 days.

(21) Appl. No.: 18/604,130

(22) Filed: Mar. 13, 2024

(65) Prior Publication Data

US 2024/0272106 A1 Aug. 15, 2024

Related U.S. Application Data

(63) Continuation of application No. PCT/JP2022/026591, filed on Jul. 4, 2022.

(30) Foreign Application Priority Data

Sep. 22, 2021 (JP) ................................. 2021-154912

(51) Int. Cl.
*G01N 27/12* (2006.01)
*G01N 33/00* (2006.01)

(52) U.S. Cl.
CPC ....... *G01N 27/122* (2013.01); *G01N 33/0031* (2013.01); *G01N 33/005* (2013.01); *G01N 33/0073* (2013.01)

(58) Field of Classification Search
CPC ............. G01N 27/12; G01N 2030/025; G01N 2001/2223; G01N 1/24; G01N 2291/0256;

(Continued)

(56) References Cited

U.S. PATENT DOCUMENTS

| | | | | |
|---|---|---|---|---|
| 10,281,420 B2* | 5/2019 | Muraoka | .............. | G01N 27/125 |
| 10,365,259 B2* | 7/2019 | Homma | ............... | G01N 33/005 |

(Continued)

FOREIGN PATENT DOCUMENTS

| | | | | |
|---|---|---|---|---|
| CN | 118661095 A | * | 9/2024 | ............. G01N 27/12 |
| JP | 2009-276309 A | | 11/2009 | |

OTHER PUBLICATIONS

International Search Report dated Aug. 30, 2022 issued in International Patent Application No. PCT/JP2022/026591, with English translation.

*Primary Examiner* — Andre J Allen
(74) *Attorney, Agent, or Firm* — Rimon P.C.

(57) ABSTRACT

A hydrogen detection device includes a hydrogen sensor and a detection circuit, wherein the hydrogen sensor includes: a first electrode; a second electrode; a metal oxide layer; a first insulating film (insulating film); a first terminal and a second terminal that are connected, through a via, to an other surface of the second electrode opposite a principal surface of the second electrode; and a third terminal connected, through a via, to an other surface of the first electrode opposite a principal surface of the first electrode, and the detection circuit includes: an ammeter that measures (1) a first resistance value between the first terminal and the second terminal and (2) a second resistance value between the third terminal and at least one of the first terminal or the second terminal; and a control circuit that selectively outputs one of the first resistance value or the second resistance value.

20 Claims, 12 Drawing Sheets

(58) Field of Classification Search
CPC .. G01N 27/121; G01N 29/036; G01N 29/022;
G01N 33/0031; G01N 33/497; G01N
27/16; G01N 19/10; G01N 1/2202; G01N
15/0656; G01N 30/30; G01N 27/4077;
G01N 21/3504; G01N 33/0009; G01N
30/12; G01N 1/2273; G01N 33/0011;
G01N 33/0006; G01N 33/4972; G01N
1/2205; G01N 30/88; G01N 33/005;
G01N 25/62; G01N 27/407; G01N
33/004; G01N 1/22; G01N 1/405; G01N
30/32; G01N 1/2252; G01N 2291/0423;
G01N 29/024; G01N 21/1702; G01N
33/0047; G01N 27/18; G01N 33/0016;
G01N 27/185; G01N 27/223; G01N
33/0037; G01N 1/2214; G01N 30/7206;
G01N 30/6095; G01N 15/06; G01N
30/20; G01N 27/122; G01N 27/74; G01N
33/0004; G01N 2291/02809; G01N
30/66; G01N 2291/0426; G01N 30/06;
G01N 2015/0046; G01N 1/2247; G01N
25/56; G01N 2030/3084; G01N 30/461;
G01N 1/2208; G01N 2291/0427; G01N
2021/1704; G01N 2201/022; G01N
30/16; G01N 1/2226; G01N 27/225;
G01N 27/419; G01N 29/222; G01N
33/0027; G01N 27/4071; G01N 15/0618;
G01N 27/4065; G01N 2291/0215; G01N
2291/02818; G01N 2291/014; G01N
25/18; G01N 33/0014; G01N 1/40; G01N
27/4067; G01N 2291/0255; G01N
30/466; G01N 2030/324; G01N 30/24;
G01N 27/126; G01N 33/0062; G01N
33/225; G01N 30/463; G01N 2030/8881;
G01N 25/68; G01N 2001/2264; G01N
27/127; G01N 30/08; G01N 27/4175;
G01N 2291/02836; G01N 33/0036; G01N
15/0255; G01N 1/38; G01N 15/065;
G01N 2030/085; G01N 33/0001; G01N
7/10; G01N 2291/021; G01N 1/26; G01N
7/00; G01N 2291/02881; G01N 27/4074;
G01N 30/62; G01N 2030/121; G01N
9/002; G01N 30/74; G01N 29/30; G01N
30/02; G01N 30/00; G01N 30/84; G01N
27/125; G01N 33/007; G01N 2030/8854;
G01N 30/78; G01N 30/40; G01N
30/8624; G01N 2291/0422; G01N
27/048; G01N 274/4078; G01N 9/32;
G01N 2030/8804; G01N 27/4062; G01N
27/128; G01N 2030/126; G01N 30/468;
G01N 33/0032; G01N 30/68; G01N
1/2258; G01N 2030/8886; G01N
15/0606; G01N 2001/2229; G01N
29/326; G01N 27/4141; G01N
2030/3076; G01N 30/64; G01N 7/14;
G01N 2001/225; G01N 1/2211; G01N
2030/3007; G01N 33/0057; G01N
21/783; G01N 27/70; G01N 30/10; G01N
30/465; G01N 2291/0212; G01N 29/032;
G01N 33/0013; G01N 21/05; G01N
30/8651; G01N 2015/0261; G01N
33/0063; G01N 33/0054; G01N
2291/02845; G01N 31/12; G01N 5/02;
G01N 2030/0095; G01N 27/626; G01N
15/0266; G01N 25/64; G01N 31/222;
G01N 33/0026; G01N 2001/024; G01N
27/622; G01N 21/39; G01N 2291/02872;
G01N 2001/2261; G01N 2001/2276;
G01N 27/66; G01N 29/02; G01N 30/18;
G01N 33/0018; G01N 33/2823; G01N
2030/626; G01N 30/14; G01N 33/0073;
G01N 35/1097; G01N 2001/028; G01N
2030/122; G01N 29/2425; G01N 30/72;
G01N 2030/128; G01N 2291/106; G01N
2030/3046; G01N 27/4075; G01N
21/274; G01N 29/348; G01N 1/34; G01N
27/4045; G01N 2030/127; G01N
2030/623; G01N 2030/642; G01N
2291/0217; G01N 2030/062; G01N
30/8631; G01N 2030/3061; G01N
27/417; G01N 33/0034; G01N 33/0075;
G01N 2001/025; G01N 25/60; G01N
27/414; G01N 2030/3015; G01N
2001/4006; G01N 2291/012; G01N
25/14; G01N 30/34; G01N 33/28; G01N
9/266; G01N 1/02; G01N 25/66; G01N
27/123; G01N 30/38; G01N 30/8641;
G01N 33/00; G01N 21/85; G01N
33/2841; G01N 1/2035; G01N 11/16;
G01N 15/0272; G01N 2001/2285; G01N
27/62; G01N 2030/402; G01N
2291/02863; G01N 27/404; G01N 31/22;
G01N 33/24; G01N 15/02; G01N 22/00;
G01N 29/2418; G01N 2030/125; G01N
21/81; G01N 2291/011; G01N 2030/009;
G01N 2030/625; G01N 30/60; G01N
2291/102; G01N 27/14; G01N 30/8658;
G01N 2001/021; G01N 1/44; G01N
15/075; G01N 2001/2244; G01N
2001/2282; G01N 2030/123; G01N
25/00; G01N 30/8675; G01N 7/04; G01N
27/124; G01N 27/227; G01N 30/6047;
G01N 33/0039; G01N 33/2835; G01N
9/00; G01N 15/0205; G01N 21/76; G01N
2291/101; G01N 33/0044; G01N 1/4022;
G01N 2030/8405; G01N 1/14; G01N
1/2294; G01N 21/53; G01N 27/129;
G01N 27/221; G01N 2009/006; G01N
2030/3053; G01N 27/04; G01N 27/226;
G01N 29/22; G01N 2001/227; G01N
2001/4016; G01N 27/60; G01N 33/0042;
G01N 33/02; G01N 2291/02408; G01N
25/32; G01N 30/56; G01N 30/6052;
G01N 30/8606; G01N 33/006; G01N
33/18; G01N 27/4143; G01N 27/68;
G01N 30/54; G01N 30/6039; G01N
30/82; G01N 9/36; G01N 1/28; G01N
2015/019; G01N 2021/399; G01N
2030/383; G01N 21/33; G01N
2291/0257; G01N 29/4427; G01N
33/2829; G01N 2030/027; G01N
2030/143; G01N 2030/167; G01N
2291/0224; G01N 27/4073; G01N
27/4162; G01N 29/46; G01N 30/28;
G01N 33/4975; G01N 2030/385; G01N
29/2462; G01N 30/70; G01N 30/8603;
G01N 31/005; G01N 33/1826; G01N
35/00871; G01N 9/26; G01N 2001/2267;
G01N 2001/245; G01N 2030/884; G01N
21/031; G01N 29/4436; G01N 33/0022;

G01N 1/10; G01N 2021/1793; G01N 2030/065; G01N 2291/015; G01N 27/06; G01N 30/86; G01N 33/0049; G01N 33/241; G01N 1/4005; G01N 2015/1486; G01N 2021/1708; G01N 2030/202; G01N 21/72; G01N 21/766; G01N 21/7703; G01N 27/4148; G01N 29/42; G01N 30/6091; G01N 33/2852; G01N 21/359; G01N 29/223; G01N 30/6034; G01N 5/00; G01N 2001/2217; G01N 2001/2241; G01N 2030/3038; G01N 25/36; G01N 29/4418; G01N 30/6078; G01N 30/80; G01N 31/223; G01N 33/0067; G01N 2030/8809; G01N 21/0332; G01N 2291/02466; G01N 2291/0421; G01N 30/8693; G01N 33/2025; G01N 1/4077; G01N 2030/204; G01N 2030/205; G01N 21/31; G01N 27/00; G01N 30/8665; G01N 17/00; G01N 2001/2833; G01N 2030/201; G01N 21/15; G01N 21/59; G01N 30/6043; G01N 31/224; G01N 33/0024; G01N 33/0029; G01N 33/0098; G01N 33/98; G01N 35/1095; G01N 15/08; G01N 2021/7786; G01N 2030/185; G01N 2030/3023; G01N 21/643; G01N 27/041; G01N 27/409; G01N 27/423; G01N 29/323; G01N 9/24; G01N 30/6004; G01N 30/76; G01N 21/77; G01N 25/70; G01N 27/4072; G01N 30/8668; G01N 33/0059; G01N 2001/4033; G01N 2291/02416; G01N 29/36; G01N 33/0081; G01N 33/025; G01N 33/22; G01N 2001/2238; G01N 2001/2255; G01N 2030/3069; G01N 2030/8411; G01N 27/002; G01N 30/7233; G01N 31/00; G01N 9/30; G01N 11/08; G01N 15/1031; G01N 2030/303; G01N 2030/525; G01N 21/314; G01N 25/142; G01N 25/4873; G01N 30/8682; G01N 33/0045; G01N 33/2847; G01N 5/025; G01N 1/4055; G01N 15/0826; G01N 2021/6432; G01N 2030/6013; G01N 2030/8423; G01N 21/0303; G01N 21/534; G01N 21/64; G01N 21/8483; G01N 2291/0222; G01N 30/6069; G01N 30/7213; G01N 33/46; G01N 9/34; G01N 2001/2893; G01N 2001/4027; G01N 2030/326; G01N 2030/328; G01N 21/3518; G01N 21/37; G01N 21/61; G01N 25/48; G01N 27/22; G01N 27/4146; G01N 29/34; G01N 30/462; G01N 30/52; G01N 30/722; G01N 5/04; G01N 15/0227; G01N 2015/084; G01N 2021/3595; G01N 2030/567; G01N 2030/8435; G01N 2030/8813; G01N 22/04; G01N 2291/02827; G01N 2291/045; G01N 25/28; G01N 27/4163; G01N 27/64; G01N 29/228; G01N 30/89; G01N 33/0021; G01N 15/082; G01N 2015/0026; G01N 2021/158; G01N 2030/8417; G01N 21/3577; G01N 2291/02433; G01N 25/54; G01N 27/02; G01N 29/2437; G01N 2001/244; G01N 2030/207; G01N 2030/407; G01N

2030/685; G01N 21/6486; G01N 2291/048; G01N 25/30; G01N 29/343; G01N 29/4472; G01N 33/146; G01N 33/84; G01N 7/16; G01N 11/00; G01N 2001/007; G01N 2021/8578; G01N 2030/405; G01N 2030/8868; G01N 2035/00326; G01N 21/3554; G01N 21/6402; G01N 21/65; G01N 29/32; G01N 33/0065; G01N 33/2888; G01N 35/1079; G01N 15/10; G01N 2021/772; G01N 2027/222; G01N 2030/008; G01N 2030/524; G01N 21/552; G01N 21/6428; G01N 21/718; G01N 2201/0221; G01N 2201/08; G01N 29/2481; G01N 30/04; G01N 30/22; G01N 30/6082; G01N 30/8686; G01N 9/20; G01N 13/00; G01N 15/00; G01N 2015/0288; G01N 2030/047; G01N 2030/146; G01N 2030/746; G01N 2035/00881; G01N 21/51; G01N 21/658; G01N 25/58; G01N 27/406; G01N 33/287; G01N 33/54373; G01N 15/1459; G01N 2001/005; G01N 2015/0038; G01N 2015/0681; G01N 2021/354; G01N 2030/628; G01N 2030/8872; G01N 21/645; G01N 2291/105; G01N 25/20; G01N 25/22; G01N 27/41; G01N 29/38; G01N 30/6026; G01N 33/0052; G01N 33/383; G01N 7/02; G01N 15/1456; G01N 17/04; G01N 2001/002; G01N 2001/383; G01N 2021/3513; G01N 2021/8557; G01N 2030/165; G01N 2030/645; G01N 21/78; G01N 2291/0258; G01N 27/043; G01N 27/07; G01N 27/26; G01N 29/14; G01N 29/2412; G01N 30/50; G01N 30/58; G01N 30/8679; G01N 33/12; G01N 33/442; G01N 35/00; G01N 35/00009; G01N 15/0211; G01N 15/04; G01N 15/0625; G01N 2001/1093; G01N 2001/2279; G01N 2015/0096; G01N 2021/0346; G01N 2021/7783; G01N 2035/00237; G01N 21/9018; G01N 2201/062; G01N 2201/0696; G01N 25/50; G01N 29/449; G01N 30/8672; G01N 33/50; G01N 35/00693; G01N 1/04; G01N 2001/105; G01N 2001/242; G01N 2021/052; G01N 2021/7773; G01N 2030/208; G01N 21/17; G01N 21/45; G01N 21/94; G01N 2201/06186; G01N 2201/1211; G01N 2291/0226; G01N 25/02; G01N 27/403; G01N 29/12; G01N 29/4481; G01N 30/44; G01N 30/6073; G01N 31/10; G01N 33/36; G01N 33/493; G01N 33/92; G01N 15/0612; G01N 2001/387; G01N 2015/0011; G01N 2030/347; G01N 2030/528; G01N 2030/621; G01N 2030/77; G01N 21/55; G01N 2291/02425; G01N 2291/02854; G01N 2291/044; G01N 27/416; G01N 29/28; G01N 29/40; G01N 29/48; G01N 30/6017; G01N 30/96; G01N 33/48714; G01N 5/045; G01N 1/4044; G01N 2001/247; G01N 2009/004; G01N 2015/025; G01N 2015/0662; G01N 2015/1024; G01N 2030/0015; G01N

2030/6008; G01N 21/09; G01N 21/171;
G01N 21/532; G01N 2201/1215; G01N
2291/0253; G01N 25/72; G01N 27/045;
G01N 27/42; G01N 29/2468; G01N
30/90; G01N 33/0019; G01N 33/48;
G01N 33/4977; G01N 35/00732; G01N
9/16; G01N 1/00; G01N 2015/0092;
G01N 2021/151; G01N 2021/3545; G01N
21/21; G01N 21/4738; G01N 21/67;
G01N 21/73; G01N 2291/0289; G01N
25/4813; G01N 27/046; G01N 27/228;
G01N 27/40; G01N 27/44721; G01N
27/49; G01N 2800/042; G01N 29/046;
G01N 29/11; G01N 30/6065; G01N
30/8613; G01N 30/8644; G01N 33/0055;
G01N 33/0068; G01N 33/0095; G01N
33/14; G01N 33/1806; G01N 33/182;
G01N 33/54386; G01N 33/6893; G01N
7/18; G01N 15/042; G01N 15/0637;
G01N 2001/045; G01N 2001/248; G01N
2015/0053; G01N 2015/0873; G01N
2021/3137; G01N 2021/391; G01N
2030/045; G01N 2030/7226; G01N
2030/8859; G01N 21/27; G01N 21/43;
G01N 21/47; G01N 21/6404; G01N
21/69; G01N 21/774; G01N 2201/024;
G01N 2291/022; G01N 25/005; G01N
25/482; G01N 27/305; G01N 27/624;
G01N 2800/52; G01N 29/07; G01N
29/2443; G01N 30/42; G01N 30/6086;
G01N 30/8634; G01N 31/225; G01N
33/1833; G01N 33/1846; G01N 33/4925;
G01N 35/08; G01N 7/08; G01N 9/04;
G01N 1/16; G01N 1/18; G01N 15/0643;
G01N 15/1012; G01N 15/1434; G01N
19/00; G01N 2001/2297; G01N
2001/2826; G01N 2001/4061; G01N
2015/1493; G01N 2021/0321; G01N
2021/0385; G01N 2021/3174; G01N
2021/7776; G01N 2030/562; G01N
2030/862; G01N 2030/8845; G01N
2035/00336; G01N 21/00; G01N 21/255;
G01N 21/35; G01N 21/41; G01N
2201/0228; G01N 2201/1218; G01N
2201/127; G01N 2203/0094; G01N
2291/0254; G01N 2291/103; G01N
2560/00; G01N 27/023; G01N 27/026;
G01N 27/623; G01N 29/2406; G01N
29/245; G01N 29/2475; G01N 30/26;
G01N 30/46; G01N 30/467; G01N
30/606; G01N 30/8637; G01N 33/1886;
G01N 33/246; G01N 33/30; G01N 33/38;
G01N 33/487; G01N 33/52; G01N
35/00594; G01N 9/22; G01N 1/286;
G01N 15/0893; G01N 15/1404; G01N
2001/1018; G01N 2001/241; G01N
2001/2866; G01N 2013/003; G01N
2021/6439; G01N 2021/6482; G01N
2021/7779; G01N 2030/381; G01N
2030/765; G01N 2035/00772; G01N
2035/041; G01N 21/03; G01N 21/11;
G01N 21/276; G01N 21/3563; G01N
21/3581; G01N 21/68; G01N 21/716;
G01N 21/8507; G01N 2201/06113; G01N
2201/129; G01N 2201/1293; G01N

2203/0286; G01N 23/00; G01N 24/08;
G01N 25/12; G01N 27/005; G01N
27/021; G01N 27/308; G01N 27/4118;
G01N 29/2431; G01N 30/36; G01N
33/20; G01N 33/227; G01N 33/2811;
G01N 33/2882; G01N 33/54346; G01N
1/42; G01N 11/04; G01N 15/01; G01N
15/0806; G01N 15/088; G01N 17/002;
G01N 17/046; G01N 2001/1427; G01N
2001/205; G01N 2001/2057; G01N
2001/2235; G01N 2001/2291; G01N
2015/0277; G01N 2021/0382; G01N
2021/635; G01N 2030/285; G01N
2030/342; G01N 2030/382; G01N
2030/527; G01N 2030/647; G01N
2030/8429; G01N 2030/847; G01N
21/253; G01N 21/293; G01N 21/71;
G01N 21/80; G01N 21/84; G01N
2201/0691; G01N 2291/018; G01N
2291/024; G01N 2291/02491; G01N
25/46; G01N 25/4846; G01N 2610/00;
G01N 27/10; G01N 27/24; G01N 27/30;
G01N 27/304; G01N 27/4145; G01N
2800/56; G01N 29/043; G01N 29/075;
G01N 29/226; G01N 30/8617; G01N
30/8627; G01N 30/8689; G01N 30/95;
G01N 33/0072; G01N 33/15; G01N
33/49; G01N 33/6848; G01N 35/10;
G01N 37/00; G01N 7/06; G01N 9/06;
G01N 1/06; G01N 1/08; G01N 11/02;
G01N 11/06; G01N 15/12; G01N
15/1429; G01N 15/149; G01N 17/008;
G01N 2001/149; G01N 2001/2071; G01N
2001/4011; G01N 2001/4088; G01N
2015/0007; G01N 2015/0675; G01N
2015/0866; G01N 2021/1706; G01N
2021/1795; G01N 2021/3125; G01N
2021/536; G01N 2021/655; G01N
2021/8585; G01N 2030/386; G01N
2030/565; G01N 2035/00247; G01N
2035/00346; G01N 2035/1053; G01N
21/25; G01N 21/49; G01N 21/6408;
G01N 2201/0216; G01N 2201/12; G01N
2203/0023; G01N 25/04; G01N 25/4866;
G01N 27/007; G01N 27/28; G01N
27/286; G01N 27/3271; G01N 27/4076;
G01N 27/411; G01N 27/447; G01N
2800/085; G01N 2800/50; G01N 29/00;
G01N 29/265; G01N 29/50; G01N
30/005; G01N 30/603; G01N 30/728;
G01N 33/0093; G01N 33/03; G01N
33/205; G01N 33/222; G01N 33/34;
G01N 33/5308; G01N 33/64; G01N
35/00722; G01N 35/021; G01N 35/085;
G01N 35/1004; G01N 35/1081; G01N
35/109; G01N 9/18; G01N 1/125; G01N
11/14; G01N 15/14; G01N 2001/1025;
G01N 2001/1037; G01N 2001/2064;
G01N 2001/2288; G01N 2001/381; G01N
2001/385; G01N 2001/4038; G01N
2009/008; G01N 2011/0093; G01N
2015/0042; G01N 2015/0687; G01N
2015/086; G01N 2015/1006; G01N
2021/0325; G01N 2021/3129; G01N
2021/3155; G01N 2021/3192; G01N

2021/335; G01N 2021/3536; G01N
2021/458; G01N 2021/556; G01N
2021/6434; G01N 2021/6484; G01N
2021/7723; G01N 2021/8466; G01N
2030/042; G01N 2030/067; G01N
2030/743; G01N 2030/8441; G01N
2030/8831; G01N 2035/00158; G01N
2035/00782; G01N 2035/1018; G01N
21/01; G01N 21/211; G01N 21/29; G01N
21/63; G01N 21/6452; G01N 21/648;
G01N 21/66; G01N 21/74; G01N 22/02;
G01N 2201/0231; G01N 2201/0245;
G01N 2201/061; G01N 2201/0633; G01N
2201/084; G01N 2201/1214; G01N
2203/0051; G01N 2203/0075; G01N
2203/0282; G01N 2291/0237; G01N
2291/0251; G01N 2291/0425; G01N
23/02; G01N 23/12; G01N 24/008; G01N
25/08; G01N 25/4886; G01N 27/028;
G01N 27/4165; G01N 27/4166; G01N
27/44; G01N 27/44704; G01N 27/72;
G01N 2800/06; G01N 2800/12; G01N
2800/307; G01N 29/221; G01N 29/227;
G01N 29/24; G01N 29/341; G01N 29/44;
G01N 29/4454; G01N 29/4463; G01N
30/7266; G01N 30/861; G01N 30/8662;
G01N 31/226; G01N 33/0008; G01N
33/10; G01N 33/367; G01N 33/445;
G01N 33/5438; G01N 33/60; G01N
33/66; G01N 35/1074; G01N 1/20; G01N
15/1023; G01N 17/006; G01N 17/043;
G01N 2001/1445; G01N 2001/2232;
G01N 2001/388; G01N 2013/006; G01N
2013/025; G01N 2015/0283; G01N
2021/0389; G01N 2021/054; G01N
2021/1725; G01N 2021/1734; G01N
2021/3133; G01N 2021/3185; G01N
2021/394; G01N 2021/653; G01N
2021/7759; G01N 2021/7763; G01N
2021/8411; G01N 2030/322; G01N
2030/889; G01N 2035/00455; G01N
2035/0097; G01N 2035/0441; G01N
2035/1044; G01N 21/251; G01N 21/272;
G01N 21/278; G01N 21/4133; G01N
21/431; G01N 21/75; G01N 21/7746;
G01N 2201/0214; G01N 2201/023; G01N
2201/0627; G01N 2201/0631; G01N
2201/066; G01N 2201/0693; G01N
2201/12746; G01N 2201/12792; G01N
2291/02475; G01N 23/2255; G01N
2333/21; G01N 2333/37; G01N 24/084;
G01N 25/4893; G01N 25/52; G01N
2500/00; G01N 27/025; G01N 27/20;
G01N 27/38; G01N 27/4111; G01N
27/4114; G01N 27/413; G01N 27/92;
G01N 2800/04; G01N 2800/2821; G01N
2800/347; G01N 2800/60; G01N 29/04;
G01N 29/0609; G01N 3/60; G01N
30/7293; G01N 30/92; G01N 33/06;
G01N 33/143; G01N 33/26; G01N
33/2876; G01N 33/388; G01N 33/48707;
G01N 33/54306; G01N 33/54366; G01N
33/57515; G01N 35/00613; G01N
35/0092; G01N 35/0099; G01N 35/04;
G01N 1/2813; G01N 1/312; G01N

11/162; G01N 13/02; G01N 13/04; G01N
15/1468; G01N 17/02; G01N 19/04;
G01N 19/08; G01N 2001/027; G01N
2001/1043; G01N 2001/1075; G01N
2001/1081; G01N 2001/1418; G01N
2001/1454; G01N 2001/2014; G01N
2001/2078; G01N 2001/282; G01N
2001/386; G01N 2001/4094; G01N
2009/028; G01N 2011/0066; G01N
2013/0225; G01N 2015/0003; G01N
2015/003; G01N 2015/0049; G01N
2015/0846; G01N 2015/1027; G01N
2015/1028; G01N 2015/1415; G01N
2015/1438; G01N 2015/1497; G01N
2021/0162; G01N 2021/0193; G01N
2021/0307; G01N 2021/0314; G01N
2021/058; G01N 2021/1719; G01N
2021/1723; G01N 2021/1751; G01N
2021/1763; G01N 2021/1797; G01N
2021/258; G01N 2021/3107; G01N
2021/3148; G01N 2021/3166; G01N
2021/3177; G01N 2021/3196; G01N
2021/3531; G01N 2021/4726; G01N
2021/4761; G01N 2021/516; G01N
2021/6417; G01N 2021/6419; G01N
2021/6441; G01N 2021/6491; G01N
2021/651; G01N 2021/7706; G01N
2021/7709; G01N 2021/7726; G01N
2021/7793; G01N 2021/8416; G01N
2021/845; G01N 2021/8494; G01N
2021/8528; G01N 2021/8564; G01N
2021/8571; G01N 2021/8592; G01N
2030/002; G01N 2030/0045; G01N
2030/022; G01N 2030/162; G01N
2030/388; G01N 2030/445; G01N
2030/8447; G01N 2030/8452; G01N
2030/8482; G01N 2030/8818; G01N
2030/8827; G01N 2030/885; G01N
2030/8863; G01N 2030/8877; G01N
2030/965; G01N 2035/00217; G01N
2035/00306; G01N 2035/00316; G01N
2035/00386; G01N 2035/00495; G01N
2035/00514; G01N 2035/00683; G01N
2035/00891; G01N 2035/009; G01N
2035/0434; G01N 2035/0437; G01N
2035/0458; G01N 2035/0484; G01N
2035/1025; G01N 2035/1039; G01N
2035/1041; G01N 2035/1055; G01N
21/07; G01N 21/13; G01N 21/1717;
G01N 21/3103; G01N 21/474; G01N
21/4788; G01N 21/553; G01N 21/554;
G01N 21/5911; G01N 21/6456; G01N
21/7743; G01N 21/86; G01N 21/9501;
G01N 2201/0236; G01N 2201/0612;
G01N 2201/0616; G01N 2201/0622;
G01N 2201/0632; G01N 2201/0636;
G01N 2201/0637; G01N 2201/0662;
G01N 2201/068; G01N 2201/0806; G01N
2201/123; G01N 2201/126; G01N
2201/12715; G01N 2201/12753; G01N
2201/12784; G01N 2201/128; G01N
2203/0007; G01N 2203/0016; G01N
2203/0033; G01N 2203/0042; G01N
2203/0048; G01N 2203/0055; G01N
2203/0057; G01N 2203/0067; G01N

2203/0092; G01N 2203/0278; G01N
2203/028; G01N 2203/0676; G01N
2223/01; G01N 2223/056; G01N
2223/613; G01N 2223/636; G01N
2223/638; G01N 2223/641; G01N
2223/652; G01N 2291/0245; G01N
2291/051; G01N 2291/056; G01N
2291/104; G01N 2291/2693; G01N
2291/2695; G01N 23/09; G01N 23/20;
G01N 23/2204; G01N 23/223; G01N
2333/35; G01N 2333/575; G01N
2333/71; G01N 2333/82; G01N
2333/916; G01N 24/006; G01N 24/082;
G01N 24/087; G01N 24/10; G01N
2405/04; G01N 2430/40; G01N 2496/70;
G01N 25/06; G01N 25/10; G01N 25/147;
G01N 25/16; G01N 25/34; G01N 25/40;
G01N 25/42; G01N 25/488; G01N
2500/10; G01N 2600/00; G01N 27/27;
G01N 27/283; G01N 27/307; G01N
27/3273; G01N 27/3275; G01N 27/3276;
G01N 27/4167; G01N 27/44708; G01N
27/44717; G01N 27/44743; G01N
27/44782; G01N 27/44791; G01N 27/76;
G01N 2800/02; G01N 2800/22; G01N
2800/24; G01N 2800/245; G01N
2800/285; G01N 2800/32; G01N 29/028;
G01N 29/048; G01N 29/0645; G01N
29/0672; G01N 29/069; G01N 29/2456;
G01N 29/2487; G01N 29/262; G01N
29/345; G01N 29/346; G01N 29/4445;
G01N 3/14; G01N 3/36; G01N 3/38;
G01N 30/6021; G01N 30/7253; G01N
30/7273; G01N 30/7286; G01N 30/8696;
G01N 30/93; G01N 30/94; G01N 31/007;
G01N 31/16; G01N 31/164; G01N
31/166; G01N 31/229; G01N 33/003;
G01N 33/0085; G01N 33/0096; G01N
33/1866; G01N 33/1893; G01N 33/2045;
G01N 33/207; G01N 33/343; G01N
33/346; G01N 33/365; G01N 33/48721;
G01N 33/48728; G01N 33/48771; G01N
33/48785; G01N 33/4905; G01N
33/5008; G01N 33/5038; G01N 33/525;
G01N 33/528; G01N 33/54388; G01N
33/54393; G01N 33/551; G01N 33/552;
G01N 33/564; G01N 33/5752; G01N
33/68; G01N 33/6806; G01N 33/6812;
G01N 33/6821; G01N 33/6842; G01N
33/6863; G01N 33/6887; G01N 33/86;
G01N 33/88; G01N 33/94; G01N
33/9453; G01N 33/9473; G01N 33/9486;
G01N 33/9493; G01N 33/96; G01N
35/00584; G01N 35/00712; G01N
35/025; G01N 35/0238; G01N 35/1009;
G01N 35/1011; G01N 35/1083; G01N
9/10; G01N 9/14; G01N 1/12; G01N
1/30; G01N 1/31; G01N 15/13; G01N
15/131; G01N 15/1433; G01N
2001/1436; G01N 2001/185; G01N
2001/222; G01N 2001/2873; G01N
2001/302; G01N 2001/4083; G01N
2011/0073; G01N 2011/147; G01N
2015/0019; G01N 2015/012; G01N
2015/016; G01N 2015/018; G01N
2015/1021; G01N 2015/1022; G01N
2015/1026; G01N 2015/1029; G01N
2015/138; G01N 2021/0106; G01N
2021/0112; G01N 2021/1731; G01N
2021/1744; G01N 2021/1761; G01N
2021/1776; G01N 2021/1785; G01N
2021/1787; G01N 2021/3144; G01N
2021/317; G01N 2021/3181; G01N
2021/392; G01N 2021/396; G01N
2021/4707; G01N 2021/4711; G01N
2021/4792; G01N 2021/5957; G01N
2021/5969; G01N 2021/632; G01N
2021/633; G01N 2021/6469; G01N
2021/6497; G01N 2021/8405; G01N
2021/8887; G01N 2021/945; G01N
2030/387; G01N 2035/00356; G01N
2035/00524; G01N 2035/0094; G01N
2035/1032; G01N 21/23; G01N 21/453;
G01N 21/538; G01N 21/5907; G01N
21/636; G01N 21/88; G01N 21/8851;
G01N 22/005; G01N 2201/025; G01N
2201/0621; G01N 2201/0668; G01N
2201/067; G01N 2201/105; G01N
2201/1288; G01N 2203/0025; G01N
2203/0032; G01N 2203/0087; G01N
2291/0228; G01N 2291/0231; G01N
2291/0235; G01N 23/046; G01N 23/06;
G01N 23/10; G01N 23/203; G01N 23/22;
G01N 23/227; G01N 23/2273; G01N
2240/38; G01N 2458/15; G01N 25/4806;
G01N 25/4826; G01N 2570/00; G01N
27/3278; G01N 27/44795; G01N 27/48;
G01N 27/605; G01N 27/87; G01N 3/24;
G01N 3/317; G01N 33/0083; G01N
33/0091; G01N 33/1813; G01N 33/186;
G01N 33/202; G01N 33/2028; G01N
33/44; G01N 33/483; G01N 33/48735;
G01N 33/53; G01N 33/5302; G01N
33/575; G01N 33/57525; G01N
33/57535; G01N 33/57555; G01N
33/6896; G01N 33/9406; G01N
35/00603; G01N 35/1016; G01N 37/005;
G01N 9/12

USPC .................................................. 73/23.2–31.7
See application file for complete search history.

(56)                    References Cited

U.S. PATENT DOCUMENTS

| | | | | |
|---|---|---|---|---|
| 10,408,779 | B2 * | 9/2019 | Wei | G01N 27/125 |
| 10,794,848 | B2 * | 10/2020 | Homma | G01N 27/128 |
| 12,158,459 | B2 * | 12/2024 | Homma | G01N 27/125 |
| 2017/0241933 | A1 * | 8/2017 | Fujii | G01N 33/005 |
| 2017/0307556 | A1 * | 10/2017 | Muraoka | G01N 33/0031 |
| 2024/0361267 | A1 * | 10/2024 | Katayama | G01N 27/045 |
| 2025/0116623 | A1 * | 4/2025 | Homma | G01N 33/005 |

* cited by examiner

Start

S10
Detect hydrogen in horizontal mode

S11
Hydrogen concentration > Threshold?    No

Yes

S12
Detect hydrogen in vertical mode

End

| 20a | 100a | 20c |
|-----|------|-----|

TE1

BE

TE2

TE1

BE

TE2

200

Detection
circuit 20b     100b

| 21a | 110a | 21c |
|-----|------|-----|

HYDROGEN DETECTION DEVICE AND CONTROL METHOD FOR HYDROGEN DETECTION DEVICE

CROSS REFERENCE TO RELATED APPLICATIONS

This is a continuation application of PCT International Application No. PCT/JP2022/026591 filed on Jul. 4, 2022, designating the United States of America, which is based on and claims priority of Japanese Patent Application No. 2021-154912 filed on Sep. 22, 2021. The entire disclosures of the above-identified applications, including the specifications, drawings and claims are incorporated herein by reference in their entirety.

FIELD

The present disclosure relates to a hydrogen detection device and a control method for a hydrogen detection device, and relates in particular to a wide-range hydrogen detection device that detects low- and high-concentration hydrogen.

BACKGROUND

A wide-range hydrogen detection device that detects low- and high-concentration hydrogen has been conventionally proposed (see Patent Literature (PTL) 1, for example). According to the technique disclosed in PTL 1, a leak detection means has two modes, a leak detection mode and a gas concentration measurement mode. This is to eliminate the waiting time caused by fatigue of the gas sensor.

CITATION LIST

Patent Literature

PTL 1: Japanese Unexamined Patent Application Publication No. 2009-276309

SUMMARY

Technical Problem

The technique disclosed in PTL 1, however, requires a valve to switch flow paths between supply of a sample gas to a first gas sensor and a background gas to a second gas sensor and supply of the sample gas to the second gas sensor and the background gas to the first gas sensor. This increases the size of the hydrogen detection device.

In view of the above, the present disclosure aims to provide a compact and wide-range hydrogen detection device etc. that detects low- and high-concentration hydrogen.

Solution to Problem

In order to achieve the above, a hydrogen detection device according to an aspect of the present disclosure is a hydrogen detection device including: a first hydrogen sensor and a second hydrogen sensor that detect hydrogen; and a first detection circuit connected to the first hydrogen sensor and the second hydrogen sensor, wherein the first hydrogen sensor includes: a first electrode including a principal surface and a second electrode including a principal surface, the principal surface of the first electrode and the principal surface of the second electrode facing each other; a first metal oxide layer in contact with the principal surface of the first electrode and the principal surface of the second electrode; a first insulating film covering the first electrode, the second electrode, and the first metal oxide layer; a first terminal and a second terminal that are connected, through a via, to an other surface of the second electrode opposite the principal surface of the second electrode; and a third terminal connected, through a via, to an other surface of the first electrode opposite the principal surface of the first electrode, the first insulating film includes, between the first terminal and the second terminal in plan view of the second electrode, a first opening where the other surface of the second electrode is exposed and not covered by the first insulating film, the second hydrogen sensor includes: a third electrode including a principal surface and a fourth electrode including a principal surface, the principal surface of the third electrode and the principal surface of the fourth electrode facing each other; a second metal oxide layer in contact with the principal surface of the third electrode and the principal surface of the fourth electrode; a second insulating film covering the third electrode, the fourth electrode, and the second metal oxide layer; a fourth terminal and a fifth terminal that are connected, through a via, to an other surface of the fourth electrode opposite the principal surface of the fourth electrode; and a sixth terminal connected, through a via, to an other surface of the third electrode opposite the principal surface of the third electrode, the second insulating film includes, between the fourth terminal and the fifth terminal in plan view of the fourth electrode, a second opening where the other surface of the fourth electrode is exposed and not covered by the second insulating film, and the first detection circuit includes: a first measurement circuit that measures a first resistance value between the first terminal and the second terminal and a second resistance value between the sixth terminal and at least one of the fourth terminal or the fifth terminal.

In order to achieve the above, a control method for a hydrogen detection device according to an aspect of the present disclosure is a control method for the hydrogen detection device described above, and includes the following performed by the first detection circuit: obtaining the first resistance value; and selectively outputting one of the first resistance value or the second resistance value, based on the first resistance value obtained.

Advantageous Effects

The present disclosure provides a compact and wide-range hydrogen detection device etc. that detects low- and high-concentration hydrogen.

BRIEF DESCRIPTION OF DRAWINGS

These and other advantages and features will become apparent from the following description thereof taken in conjunction with the accompanying Drawings, by way of non-limiting examples of embodiments disclosed herein.

FIG. 9 is a block diagram illustrating a configuration example of a hydrogen detection device according to Variation 3 of the embodiment.

FIG. 10 is a block diagram illustrating a configuration example of a hydrogen detection device according to Variation 4 of the embodiment.

DESCRIPTION OF EMBODIMENT

Figure 1A:
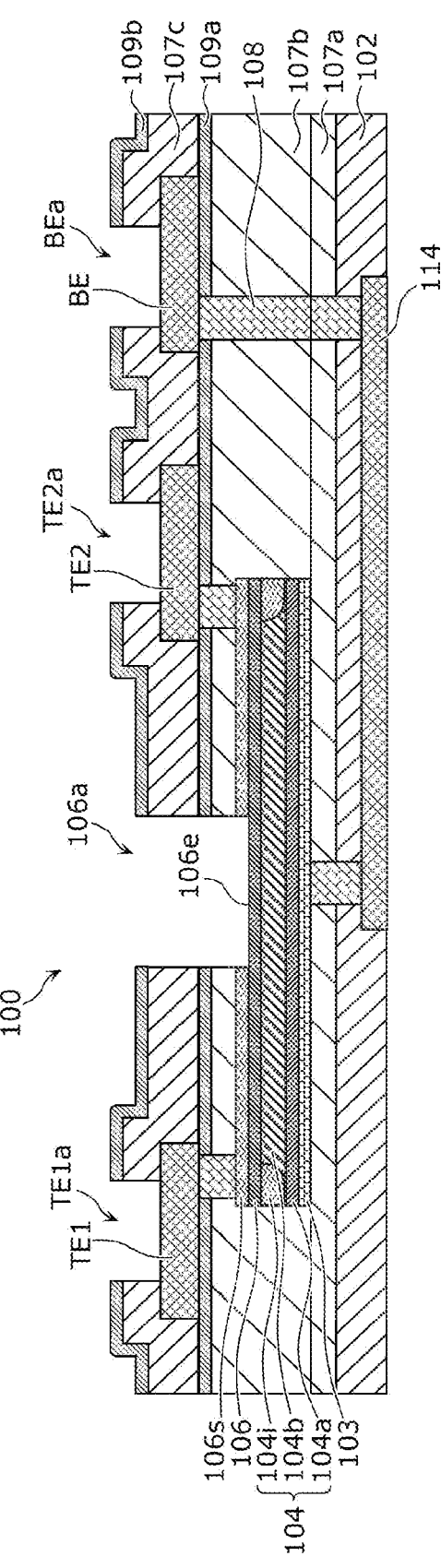
FIG. 1A is a cross-sectional view illustrating a configuration example of a hydrogen sensor according to an embodiment.

Hereinafter, an embodiment of the present disclosure will be described in detail with reference to the drawings. Note that the embodiment described below illustrates a specific example of the present disclosure. The numerical values, shapes, materials, constituent elements, the arrangement and connection of the constituent elements, steps, the processing order of the steps, etc. illustrated in the embodiment below are mere examples, and are not intended to limit the present disclosure. The drawings are not necessarily precise illustrations. In the drawings, constituent elements that are essentially the same share like reference signs, and duplicate descriptions thereof are omitted or simplified.

Figure 1B:
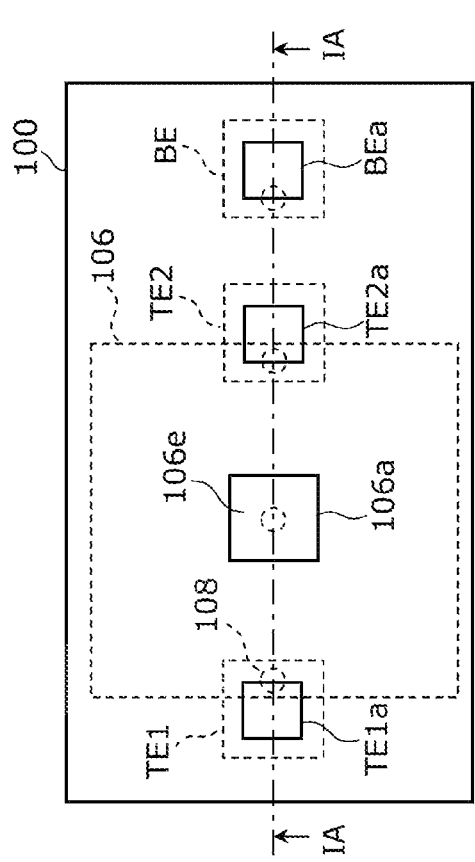
FIG. 1B is a top view illustrating a configuration example of the hydrogen sensor according to the embodiment.

FIG. 1A is a cross-sectional view illustrating a configuration example of hydrogen sensor 100 according to the embodiment. FIG. 1B is a top view illustrating a configuration example of hydrogen sensor 100 according to the embodiment. Note that FIG. 1A illustrates a schematic cross section along line IA-IA of FIG. 1B, viewed in the arrow direction.

Hydrogen sensor 100 is a minute structure which can be manufactured by a semiconductor manufacturing process. Hydrogen sensor 100 is a wide-range hydrogen sensor that detects low- and high-concentration hydrogen and includes, as key structural components: first electrode 103 including a principal surface and second electrode 106 including a principal surface, the principal surface of first electrode 103 and the principal surface of second electrode 106 facing each other; metal oxide layer 104 in contact with the principal surface of first electrode 103 and the principal surface of second electrode 106; insulating films 107a to 107c, 109a, and 109b covering first electrode 103, second electrode 106, and metal oxide layer 104; first terminal TE1 and second terminal TE2 that are connected, through a via, to an other surface of second electrode 106 opposite the principal surface of second electrode 106; and third terminal BE connected, through a via, to an other surface of first electrode 103 opposite the principal surface of first electrode 103. Insulating film 107b includes, between first terminal TE1 and second terminal TE2 in plan view of second electrode 106, opening 106a where the other surface of second electrode 106 is exposed and not covered by insulating film 107b.

First electrode 103 is a planar electrode and includes two surfaces. Of the two surfaces of first electrode 103, one surface (i.e., the upper surface in FIG. 1A) is in contact with metal oxide layer 104, and the other surface (i.e., the lower surface in FIG. 1A) is in contact with insulating film 107a and via 108. In FIG. 1B, first electrode 103 is in a rectangular shape of the same size as that of second electrode 106. First electrode 103 may include, for example, a material having a standard electrode potential lower than that of metals forming metal oxides, such as tungsten, nickel, tantalum, titanium, aluminum, tantalum nitride, and titanium nitride. The higher the value of the standard electrode potential is, the more resistant to oxidation the material is. First electrode 103 in FIG. 1A is formed with, for example, transition metal nitride such as tantalum nitride (TaN) or titanium nitride (TIN), or a lamination thereof.

Metal oxide layer 104 is sandwiched between the principal surface of first electrode 103 and the principal surface of second electrode 106 facing each other, is formed with a metal oxide serving as a gas-sensitive resistance film, and has a resistance value that reversibly changes according to the presence and absence of a hydrogen-containing gas in a gas in contact with second electrode 106. It suffices so long as metal oxide layer 104 has a property that its resistance is changed by hydrogen. Metal oxide layer 104 is formed with an oxygen-deficient metal oxide, for example. As the base metal of metal oxide layer 104, at least one of the following may be selected: aluminum (Al) and transition metals such as tantalum (Ta), hafnium (Hf), titanium (Ti), zirconium (Zr), niobium (Nb), tungsten (W), nickel (Ni), and iron (Fe).

Since transition metals can take on plural oxidation states, different resistance states can be realized through redox reactions. Here, the "degree of oxygen deficiency" of a metal oxide is the ratio of deficiency of oxygen in the metal oxide to the amount of oxygen in an oxide having a stoichiometric composition composed of the same elements as those of the metal oxide. Here, the deficiency of oxygen is a value obtained by subtracting the amount of oxygen in the metal oxide from the amount of oxygen in the metal oxide having a stoichiometric composition. If there can be two or more metal oxides having stoichiometric compositions composed of the same elements as those of the metal oxide, the degree of oxygen deficiency of the metal oxide is defined based on one of the two or more metal oxides having stoichiometric compositions that has the highest resistance value. Metal oxides having stoichiometric compositions are more stable and higher in resistance value than metal oxides having other compositions.

For example, when the base metal of metal oxide layer 104 is tantalum (Ta), the oxide having a stoichiometric composition as defined above is $Ta_2O_5$, so metal oxide layer 104 can be expressed as $TaO_{2.5}$. The degree of oxygen deficiency of $TaO_{2.5}$ is 0%, and the degree of oxygen deficiency of $TaO_{1.5}$ is (2.5-1.5)/2.5=40%. The degree of oxygen deficiency of a metal oxide with excess oxygen is a negative value. Note that in the present disclosure, the degree of oxygen deficiency can take a positive value, 0, or a negative value unless otherwise noted. An oxide with a low degree of oxygen deficiency has a high resistance value because it is closer to an oxide having a stoichiometric composition, whereas an oxide with a high degree of oxygen deficiency has a low resistance value because it is closer to the metal forming the oxide.

Metal oxide layer 104 illustrated in FIG. 1A includes: first layer 104a in contact with first electrode 103; second layer 104b in contact with first layer 104a and second electrode 106; and isolation layer 104i. The degree of oxygen deficiency of second layer 104b is lower than that of first layer 104a. For example, first layer 104a is $TaO_x$. Second layer 104b is $Ta_2O_5$ whose degree of oxygen deficiency is lower than that of first layer 104a. Metal oxide layer 104 includes isolation layer 104i at the perimeter in plan view of first electrode 103.

Here, plan view means viewing hydrogen sensor 100 according to the present disclosure from a viewpoint in the layer-stacking direction in FIG. 1A; in other words, viewing from a viewpoint in the direction normal to any of the surfaces of, for example, first electrode 103 and second electrode 106 that are planar. For example, plan view refers to viewing the top surface of hydrogen sensor 100 illustrated in FIG. 1B.

The resistance state of such metal oxide layer 104 is that the resistance value decreases according to a hydrogen-containing gas that comes into contact with second electrode 106 (i.e., when the amount of the hydrogen-containing gas increases). In detail, when a hydrogen-containing gas is present in a detection-target gas, hydrogen atoms are dissociated from the hydrogen-containing gas in second electrode 106. The dissociated hydrogen atoms enter metal oxide layer 104 and form impurity levels. In particular, the dissociated hydrogen atoms concentrate in the vicinity of the interface with second electrode 106, making the apparent thickness of second layer 104b smaller. As a result, the resistance value of metal oxide layer 104 decreases.

Second electrode 106 is a planar electrode with hydrogen dissociability, and includes two surfaces. Of the two surfaces of second electrode 106, one surface (i.e., the lower surface in FIG. 1A) is in contact with metal oxide layer 104, and the other surface (i.e., the upper surface in FIG. 1A) is in contact with metal layer 106s and the outside air. Second electrode 106 has, in opening 106a, exposed portion 106e that is exposed to the outside air. Second electrode 106 is formed with a material that catalyzes dissociation of hydrogen atoms from gas molecules having hydrogen atoms, for example: noble metal such as platinum (Pt), iridium (Ir), or palladium (Pd); or nickel (Ni); or an alloy containing at least one of these. It is assumed that second electrode 106 in FIG. 1A is platinum (Pt). Two terminals, namely first terminal TE1 and second terminal TE2, are connected to second electrode 106.

First terminal TE1 is connected to second electrode 106 through via 108.

Second terminal TE2 is connected to second electrode 106 through via 108. First terminal TE1 and second terminal TE2 are connected to an external detection circuit that drives hydrogen sensor 100, through opening TE1a and opening TE2a, respectively.

As illustrated in FIG. 1B, first terminal TE1 and second terminal TE2 are disposed at positions between which exposed portion 106e is interposed in plan view of second electrode 106. With first terminal TE1 and second terminal TE2 disposed in this manner, application of a predetermined voltage between first terminal TE1 and second terminal TE2 causes passage of current through exposed portion 106e of second electrode 106, that is, causes current to flow through exposed portion 106e. The passage of current through exposed portion 106e of second electrode 106 is considered to activate the hydrogen dissociation by exposed portion 106e. Note that the predetermined voltage may be voltages that are opposite to each other in polarity.

In hydrogen sensor 100, the resistance value between first terminal TE1 and second terminal TE2 changes when gas molecules containing hydrogen atoms come into contact with exposed portion 106e during the passage of current through exposed portion 106e. By the above detection circuit detecting this change in resistance value (this detection is also referred to as the "horizontal mode"), gas molecules containing low-concentration hydrogen atoms are detected.

Third terminal BE is connected to first electrode 103 through opening BEa, via 108, wiring 114, and via 108. Third terminal BE is connected, through opening BEa, to the external detection circuit that drives hydrogen sensor 100. In hydrogen sensor 100, the resistance between first electrode 103 and second electrode 106 changes when gas molecules containing hydrogen atoms come into contact with exposed portion 106e during the passage of current through exposed portion 106e. In other words, in hydrogen sensor 100, the resistance value between third terminal BE and at least one of first terminal TE1 or second terminal TE2 changes when gas molecules containing hydrogen atoms come into contact with exposed portion 106e during the passage of current through exposed portion 106e. Also by the above detection circuit detecting this change in resistance value (this detection is also referred to as the "vertical mode"), gas molecules containing high-concentration hydrogen atoms are detected.

Note that insulating film 102, insulating films 107a to 107c, and insulating films 109a and 109b that cover key components of hydrogen sensor 100 are formed with a silicon oxide film, a silicon nitride film, etc.

Metal layer 106s is formed on the upper surface of second electrode 106 except for opening 106a. Metal layer 106s includes, for example, TiAlN as the material, and is formed as an etching stopper for forming vias 108, but is not essential.

The laminate of first electrode 103, metal oxide layer 104, and second electrode 106 is an element that can be used as a storage element of resistance random access memory (ReRAM). The storage element of the resistance random access memory is a digital storage element which uses two of the possible states that metal oxide layer 104 can take, namely a high-resistance state and a low-resistance state. Hydrogen sensor 100 according to the present disclosure uses the high-resistance state among the possible states of metal oxide layer 104.

FIG. 1A illustrates an example of metal oxide layer 104 having a two-layer configuration with first layer 104a that includes TaO$_x$ as the material and second layer 104b that includes, as the material, Ta$_2$O$_5$ whose degree of oxygen deficiency is low. However, metal oxide layer 104 may have a one-layer configuration having, as the material, TaO$_x$ or Ta$_2$O$_5$ whose degree of oxygen deficiency is low.

Figure 2A:
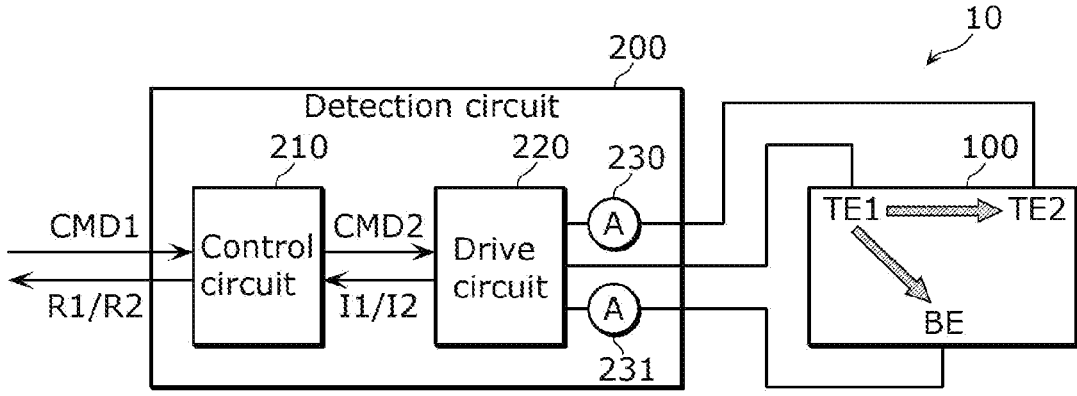
FIG. 2A is a block diagram illustrating a configuration example of a hydrogen detection device according to the embodiment.

FIG. 2A is a block diagram illustrating a configuration example of hydrogen detection device 10 according to the embodiment. Hydrogen detection device 10 is a wide-range hydrogen detection device that detects low- and high-concentration hydrogen by dynamically and selectively driving hydrogen sensor 100 illustrated in FIG. 1A and FIG. 1B, either in the horizontal mode or in the vertical mode, and includes hydrogen sensor 100 illustrated in FIG. 1A and FIG. 1B and detection circuit 200 connected to hydrogen sensor 100.

Detection circuit 200 includes control circuit 210, drive circuit 220, and ammeters 230 and 231.

Ammeter 230 is a measurement circuit that measures the current flowing in hydrogen sensor 100 in the horizontal mode, that is, the current flowing between first terminal TE1 and second terminal TE2 of hydrogen sensor 100.

Ammeter 231 is a measurement circuit that measures the current flowing in hydrogen sensor 100 in the vertical mode, that is, the current flowing between third terminal BE of hydrogen sensor 100 and at least one of first terminal TE1 or second terminal TE2 of hydrogen sensor 100.

Figure 2B:
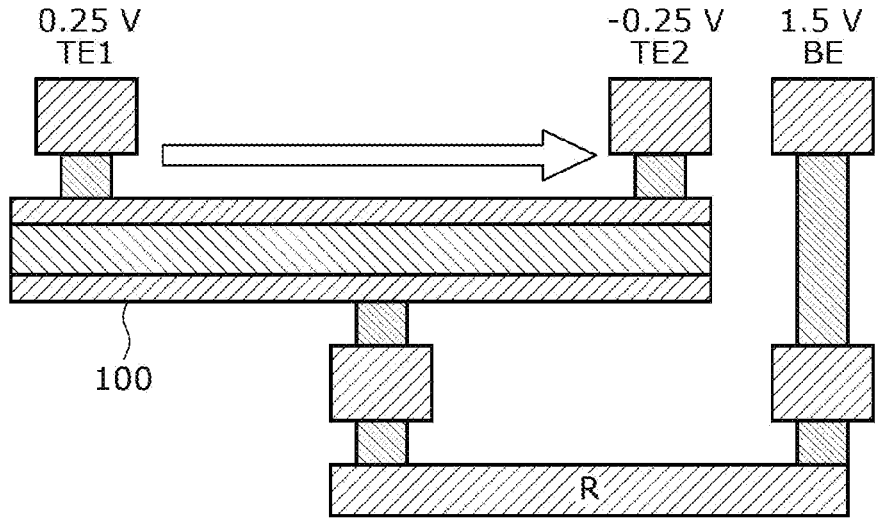
FIG. 2B is a diagram illustrating an example of voltage application when the hydrogen detection device illustrated in FIG. 2A is driven in the horizontal mode.
Figure 2C:
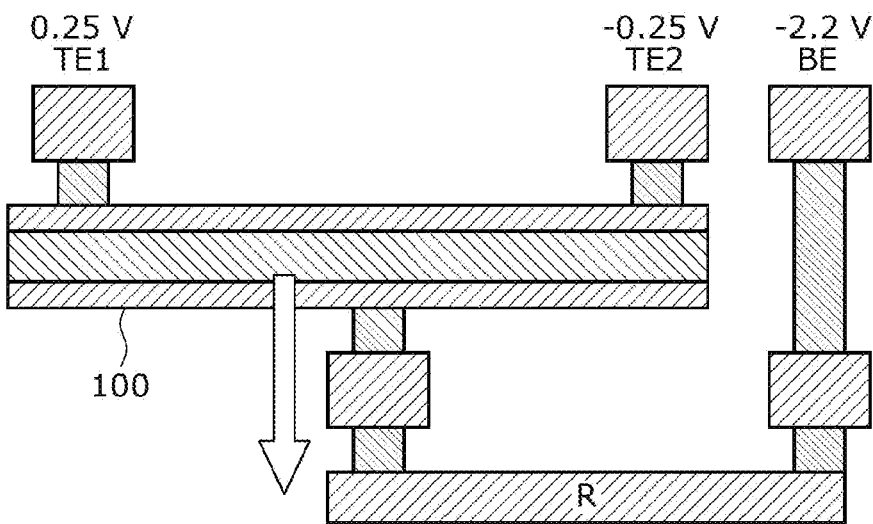
FIG. 2C is a diagram illustrating an example of voltage application when the hydrogen detection device illustrated in FIG. 2A is driven in the vertical mode.

In the case of driving hydrogen sensor 100 in the horizontal mode according to instruction CMD2 provided from control circuit 210, drive circuit 220 reads the value of current (current value I1) flowing in ammeter 230 in the state where the potentials (0.25 V, −0.25 V, and 1.5 V) illustrated in FIG. 2B are applied to first terminal TE1, second terminal TE2, and third terminal BE, respectively, and returns current value I1 which has been read to control circuit 210. On the other hand, in the case of driving hydrogen sensor 100 in the vertical mode, drive circuit 220 reads the value of current (current value I2) flowing in ammeter 231 in the state where the potentials (0.25 V, −0.25 V, and −2.2 V) illustrated in FIG. 2C are applied to first terminal TE1, second terminal TE2, and third terminal BE, respectively, and returns current value I2 which has been read to control circuit 210. Note that the applied voltages illustrated in FIG. 2B and FIG. 2C are mere examples and are not limited to such values.

When control circuit 210 receives instruction CMD1 from an external source, control circuit 210 dynamically determines, using hydrogen sensor 100, the mode (horizontal mode/vertical mode) suitable for the current hydrogen concentration by communicating with drive circuit 220, calculates the resistance value (R1 or R2) of hydrogen sensor 100 in the determined mode, and outputs the calculated resistance value to an external source. Specifically, control circuit 210 calculates the resistance value (R1 or R2) of hydrogen sensor 100 based on the current value (I1 or I2) obtained from drive circuit 220 and the values of voltage that drive circuit 220 has applied to hydrogen sensor 100. Note that control circuit 210 may include, for example, memory in which a program is stored and a processor that executes the program, or may be a logic circuit/sequencer that sequentially executes processes according to instruction CMD1 provided from the external source. Control circuit 210 may output, instead of, or together with, the resistance value of hydrogen sensor 100, the hydrogen concentration converted from the resistance value of hydrogen sensor 100.

Figure 3A:
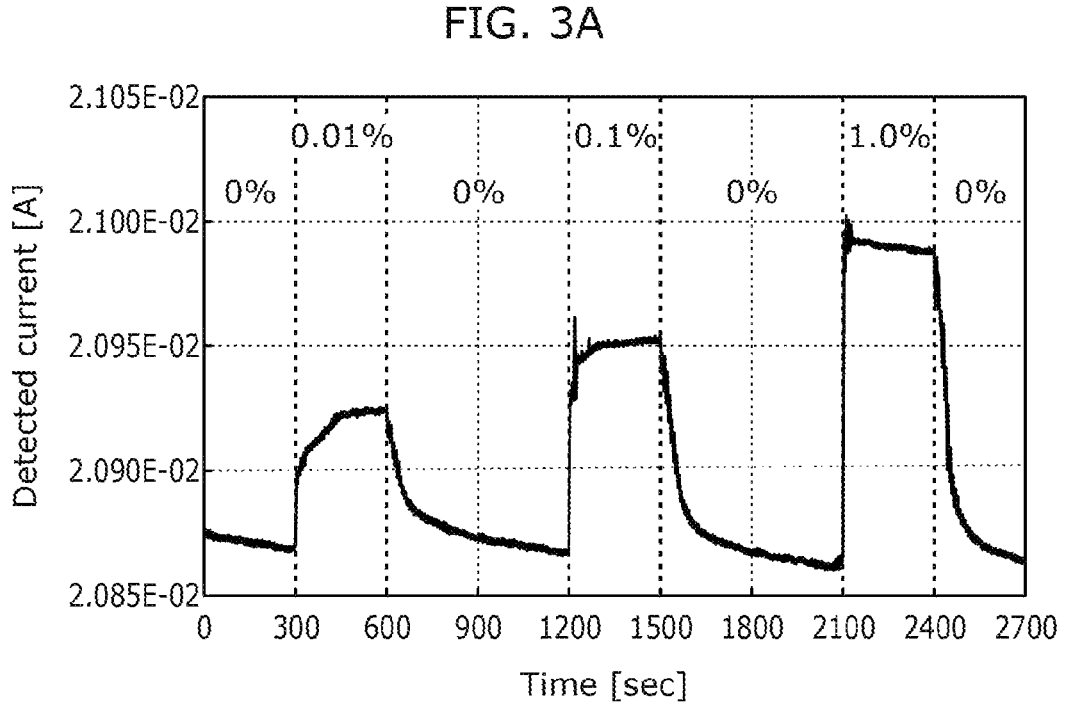
FIG. 3A is a diagram illustrating an example of actual measurement (the waveform of detected current) performed in the horizontal mode by the hydrogen detection device according to the embodiment.
Figure 3B:
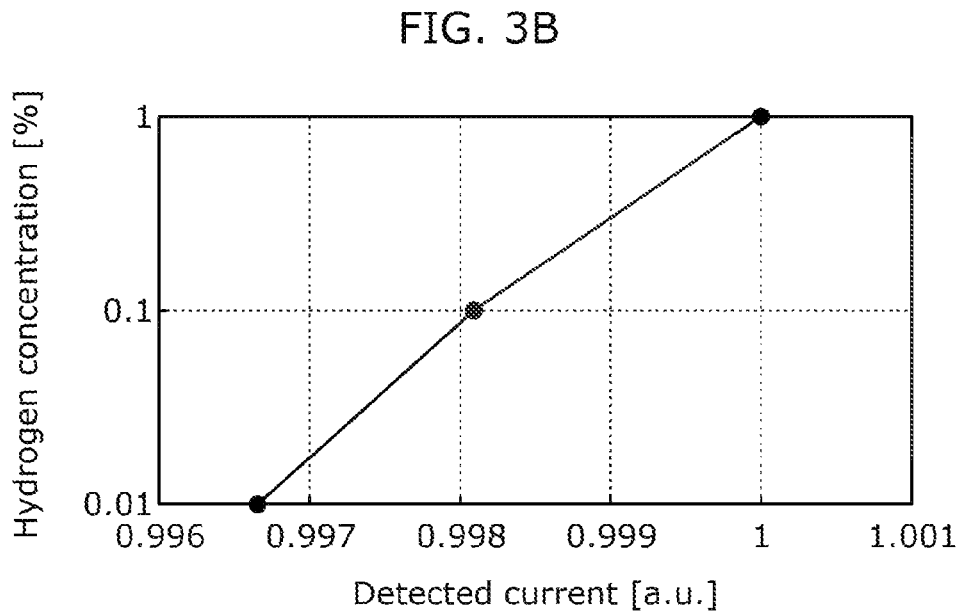
FIG. 3B is a graph illustrating the relationship between the detected current obtained in FIG. 3A (the horizontal axis) and hydrogen concentration at that time (the vertical axis).

FIG. 3A is a diagram illustrating an example of actual measurement (the waveform of detected current obtained by ammeter 230) performed in the horizontal mode by hydrogen detection device 10 according to the embodiment. FIG. 3B is a graph illustrating the relationship between the detected current obtained in FIG. 3A (the horizontal axis) and hydrogen concentration at that time (the vertical axis). As illustrated in FIG. 3A, in this example, hydrogen sensor 100 is intermittently exposed three times to hydrogen of predetermined concentrations (0.01%, 0.1%, and 1.0% from the left). FIG. 3B plots points corresponding to the current flowing through hydrogen sensor 100 in the horizontal mode during hydrogen exposure in FIG. 3A and the hydrogen concentration at that time. Note that the values of hydrogen concentration are in percentage (%) of the gas volume ratio.

Figures 4A, 4B:
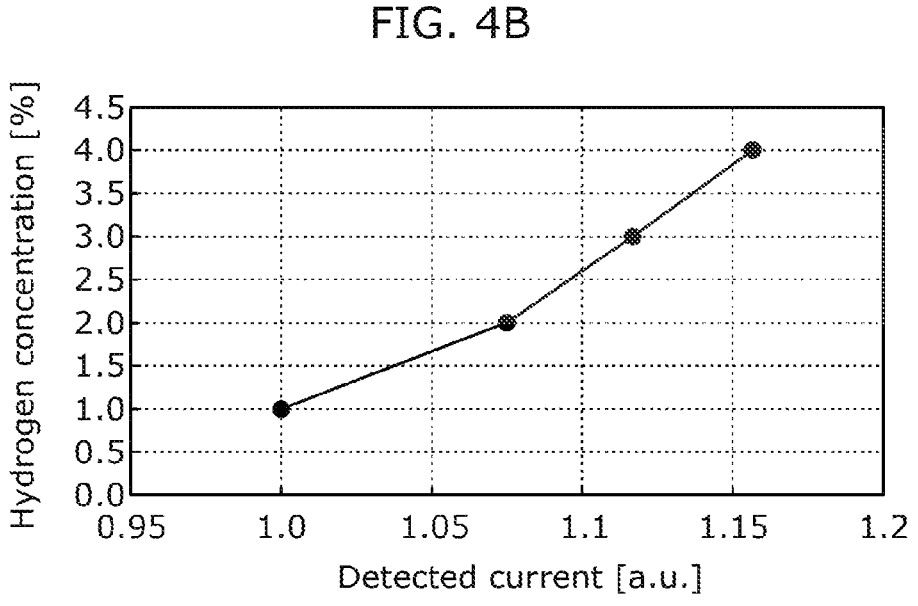
FIG. 4A is a diagram illustrating an example of actual measurement (the waveform of detected current) performed in the vertical mode by the hydrogen detection device according to the embodiment.
FIG. 4B is a graph illustrating the relationship between the detected current obtained in FIG. 4A (the horizontal axis) and hydrogen concentration at that time (the vertical axis).

FIG. 4A is a diagram illustrating an example of actual measurement (the waveform of detected current obtained by ammeter 231) performed in the vertical mode by hydrogen detection device 10 according to the embodiment. FIG. 4B is a graph illustrating the relationship between the detected current obtained in FIG. 4A (the horizontal axis) and hydrogen concentration at that time (the vertical axis). As illustrated in FIG. 4A, in this example, hydrogen sensor 100 is intermittently exposed four times to hydrogen of predetermined concentrations (1.0%, 2.0%, 3.0%, and 4.0% from the left). FIG. 4B plots points corresponding to the current flowing through hydrogen sensor 100 in the vertical mode during hydrogen exposure in FIG. 4A and the hydrogen concentration at that time.

As can be seen from FIGS. 3A and 3B illustrating the characteristics of hydrogen sensor 100 in the horizontal mode and FIGS. 4A and 4B illustrating the characteristics of hydrogen sensor 100 in the vertical mode (particularly from the vertical axes of FIG. 3B and FIG. 4B), in the horizontal mode, for hydrogen of low concentrations including the range of from 0.01% to 1%, the detected current increases substantially linearly with respect to the logarithmic increase in concentration. On the other hand, in the vertical mode, for hydrogen of high concentrations including the range of from 1.0% to 4.0%, the detected current increases substantially in proportion to the concentration. That is to say, hydrogen sensor 100 detects low-concentration hydrogen in the horizontal mode and high-concentration hydrogen in the vertical mode. Note that in the horizontal mode, hydrogen sensor 100 detects hydrogen of low concentrations exceeding the concentration range illustrated in FIG. 3B, and in the vertical mode, hydrogen sensor 100 detects hydrogen of high concentrations exceeding the concentration range illustrated in FIG. 4B.

Figure 5:
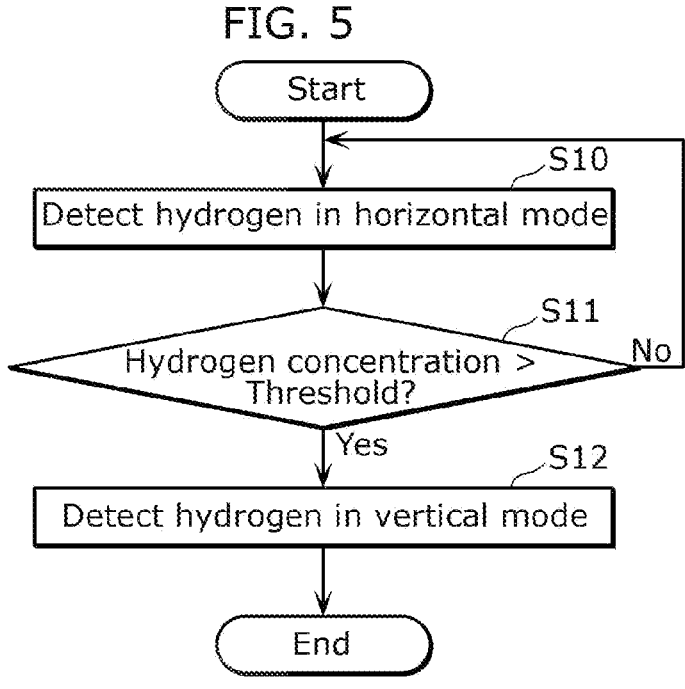
FIG. 5 is a flowchart illustrating an example of operation of the hydrogen detection device illustrated in FIG. 2A (a control method for the hydrogen detection device).

FIG. 5 is a flowchart illustrating an example of operation of hydrogen detection device 10 illustrated in FIG. 2A (a control method for hydrogen detection device 10). Illustrated here is a process, performed by hydrogen detection device 10, of detecting a hydrogen concentration while dynamically switching between the horizontal mode and the vertical mode.

When control circuit 210 of hydrogen detection device 10 receives, from an external source, instruction CMD1 indicating start of detection, control circuit 210 first detects the hydrogen concentration in the horizontal mode (S10). Specifically, control circuit 210 controls drive circuit 220 to repeat, through pulse voltage drive on hydrogen sensor 100, the process of reading, via drive circuit 220, the value of current flowing through ammeter 230 (current value I1) in the state where the potentials illustrated in FIG. 2B (0.25 V, −0.25 V, and 1.5 V) are applied to first terminal TE1, second terminal TE2, and third terminal BE, respectively. Control circuit 210 calculates resistance value R1 of hydrogen sensor 100 based on current value I1 obtained from drive circuit 220 and the values of voltage that drive circuit 220 has applied to hydrogen sensor 100, and outputs the calculated resistance value (R1 or a hydrogen concentration converted from resistance value R1) to an external source.

Here, every time control circuit 210 obtains a hydrogen concentration converted from resistance value R1, control circuit 210 determines whether the hydrogen concentration is above a threshold (e.g., the hydrogen concentration of 1%) (S11).

When the determination result is that the obtained hydrogen concentration is above the threshold (e.g., the hydrogen concentration of 1%) (Yes in S11), control circuit 210 switches from the horizontal mode to the vertical mode and detects the hydrogen concentration in the vertical mode (S12). Specifically, control circuit 210 controls drive circuit 220 to repeat, through pulse voltage drive on hydrogen sensor 100, the process of reading, via drive circuit 220, the value of current flowing through ammeter 231 (current value I2) in the state where the potentials illustrated in FIG. 2C (0.25 V, −0.25 V, and −2.2 V) are applied to first terminal TE1, second terminal TE2, and third terminal BE, respectively. Control circuit 210 calculates resistance value R2 of hydrogen sensor 100 based on current value I2 obtained from drive circuit 220 and the values of voltage that drive circuit 220 has applied to hydrogen sensor 100, and outputs calculated resistance value R2 (or a hydrogen concentration converted from resistance value R2) to an external source.

On the other hand, when the obtained hydrogen concentration is not above the threshold (e.g., the hydrogen concentration of 1%) (No in S11), control circuit 210 continues the hydrogen detection in the horizontal mode.

After that, if the detected hydrogen concentration falls below the threshold (e.g., the hydrogen concentration of 1%) after the detection in the vertical mode, control circuit 210 may switch from the vertical mode to the horizontal mode.

As described above, hydrogen detection device 10 according to the present embodiment includes a first hydrogen sensor (hydrogen sensor 100) that detects hydrogen and a third detection circuit (detection circuit 200) connected to the first hydrogen sensor (hydrogen sensor 100). The first hydrogen sensor (hydrogen sensor 100) includes: first electrode 103 including a principal surface and second electrode 106 including a principal surface, the principal surface of first electrode 103 and the principal surface of second electrode 106 facing each other; a first metal oxide layer (metal oxide layer 104) disposed in contact with the principal surface of first electrode 103 and the principal surface of second electrode 106; a first insulating film (insulating films 107a to 107c etc.) covering first electrode 103, second electrode 106, and the first metal oxide layer (metal oxide layer 104); first terminal TE1 and second terminal TE2 that are connected, through via 108, to an other surface of second electrode 106 opposite the principal surface of second electrode 106; and third terminal BE connected, through via 108, to an other surface of first electrode 103 opposite the principal surface of first electrode 103. The first insulating film (insulating films 107a to 107c etc.) includes, between first terminal TE1 and second terminal TE2 in plan view of second electrode 106, a first opening (opening 106a) where the other surface of second electrode 106 is exposed and not covered by the first insulating film (insulating films 107a to 107c etc.). The third detection circuit (detection circuit 200) includes: a third measurement circuit (ammeters 230 and 231) that measures a first resistance value between first terminal TE1 and second terminal TE2 and a second resistance value between third terminal BE and at least one of first terminal TE1 or second terminal TE2; and a second control circuit (control circuit 210) that selectively outputs one of the first resistance value or the second resistance value.

Accordingly, by merely switching the driving modes for hydrogen sensor 100 that is a minute structure manufacturable by a semiconductor manufacturing process, low-concentration hydrogen and high-concentration hydrogen are detected. Unlike the conventional technology, this eliminates the need for a valve or the like that switches gas flow paths, thus realizing compact and wide-range hydrogen detection device 10 that detects low- and high-concentration hydrogen.

The second control circuit (control circuit 210) selectively outputs one of the first resistance value or the second resistance value, based on the first resistance value. Accordingly, an appropriate driving mode is dynamically determined according to the actual hydrogen concentration, and hydrogen is detected with an appropriate measurement range.

The first resistance value is more dependent on low-concentration hydrogen than the second resistance value is. Accordingly, by driving hydrogen sensor 100 in the horizontal mode in the case of detecting low-concentration hydrogen and driving hydrogen sensor 100 in the vertical mode in the case of detecting high-concentration hydrogen, hydrogen can be detected with an appropriate measurement range.

The first metal oxide layer (metal oxide layer 104) includes a transition metal oxide. First electrode 103 includes a transition metal nitride, and second electrode 106 includes noble metal. Accordingly, hydrogen detection device 10 whose resistance value sensitively changes in response to hydrogen is realized.

A control method for hydrogen detection device 10 according to the present embodiment includes the following performed by the third detection circuit (detection circuit 200): obtaining the first resistance value; and selectively outputting one of the first resistance value or the second resistance value, based on the first resistance value obtained.

Accordingly, by merely switching the driving modes for hydrogen sensor 100 which is a minute structure, low-concentration hydrogen and high-concentration hydrogen are selectively detected. Unlike the conventional technology, this eliminates the need for a valve or the like that switches gas flow paths, thus realizing a control method for compact and wide-range hydrogen detection device 10 that detects low- and high-concentration hydrogen.

Figure 6:
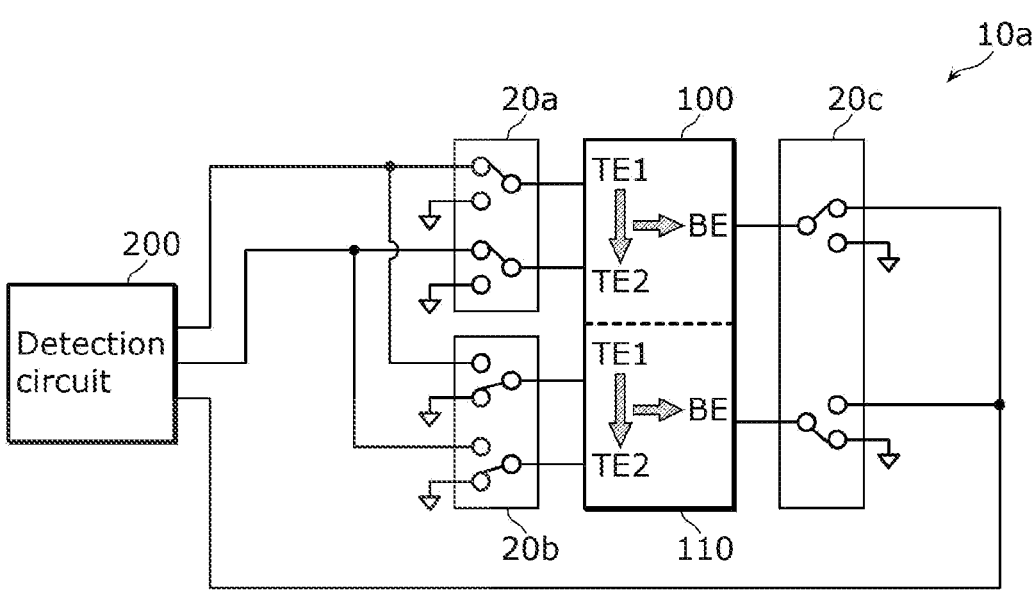
FIG. 6 is a block diagram illustrating a configuration example of a hydrogen detection device according to Variation 1 of the embodiment.

FIG. 6 is a block diagram illustrating a configuration example of hydrogen detection device 10a according to Variation 1 of the embodiment. Hydrogen detection device 10a according to the present variation includes a spare hydrogen sensor in addition to the configuration of hydrogen detection device 10 according to the embodiment. In more detail, hydrogen detection device 10a includes spare hydrogen sensor 110 and three switching circuits 20a to 20c in addition to the configuration of hydrogen detection device 10 according to the embodiment.

Spare hydrogen sensor 110 is a hydrogen sensor serving as a spare having the same structure as hydrogen sensor 100.

Each of three switching circuits 20a to 20c is a switch including two single-pole, double-throw (SPDT) switches. Switching circuit 20a switches electrical continuity and discontinuity between detection circuit 200 and first and second terminals TE1 and TE2 of hydrogen sensor 100 under the control of control circuit 210 included in detection circuit 200. Switching circuit 20b switches electrical continuity and discontinuity between detection circuit 200 and first and second terminals TE1 and TE2 of spare hydrogen sensor 110 under the control of control circuit 210 included in detection circuit 200. Switching circuit 20c switches electrical continuity and discontinuity between detection circuit 200 and third terminals BE of hydrogen sensor 100 and spare hydrogen sensor 110 under the control of control circuit 210 included in detection circuit 200.

Figure 7:
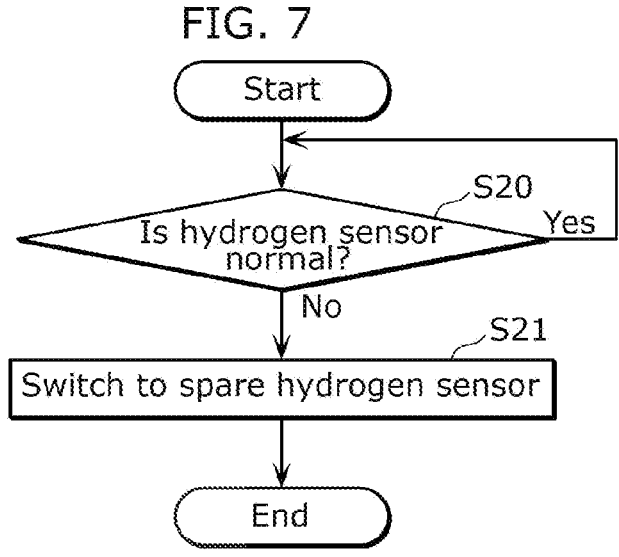
FIG. 7 is a flowchart illustrating an example of operation of the hydrogen detection device according to Variation 1 illustrated in FIG. 6.

FIG. 7 is a flowchart illustrating an example of operation of hydrogen detection device 10a according to Variation 1 illustrated in FIG. 6. Illustrated here is the process of dynamically switching the hydrogen sensor used by hydrogen detection device 10a, from hydrogen sensor 100 to spare hydrogen sensor 110.

In usual cases, control circuit 210 connects hydrogen sensor 100 to detection circuit 200 by controlling switching circuits 20a to 20c, and performs hydrogen detection as illustrated in the flowchart in FIG. 5, using hydrogen sensor 100. In parallel with the hydrogen detection, control circuit 210 determines whether hydrogen sensor 100 is normal or not (S20). Specifically, control circuit 210 determines whether hydrogen sensor 100 is normal or anomalous by determining whether the resistance value at hydrogen sensor 100 is within a predetermined range (e.g., in the horizontal mode, resistance values corresponding to a hydrogen concentration range of from 0% to 1%, and in the vertical mode, resistance values corresponding to a hydrogen concentration range of from 1.0% to 100%).

When the determination result is that hydrogen sensor 100 is normal (Yes in S20), control circuit 210 continues the hydrogen detection using hydrogen sensor 100, whereas when determining that hydrogen sensor 100 is anomalous (No in S20), control circuit 210, by controlling switching circuits 20a to 20c, switches from hydrogen sensor 100 to spare hydrogen sensor 110 as the hydrogen sensor connected to detection circuit 200 and performs the hydrogen detection using spare hydrogen sensor 110 (S21).

As described above, hydrogen detection device 10a according to Variation 1 includes, in addition to the configuration of hydrogen detection device 10 according to the embodiment, spare hydrogen sensor 110 having the same structure as the first hydrogen sensor (hydrogen sensor 100) and a third switching circuit (switching circuits 20a to 20c) that selectively connects one of the first hydrogen sensor (hydrogen sensor 100) or the spare hydrogen sensor (spare hydrogen sensor 110) to the third detection circuit (detection circuit 200). Accordingly, even when one hydrogen sensor 100 malfunctions, it is possible to continue the hydrogen detection using spare hydrogen sensor 110, thereby improving user convenience.

Figure 8:
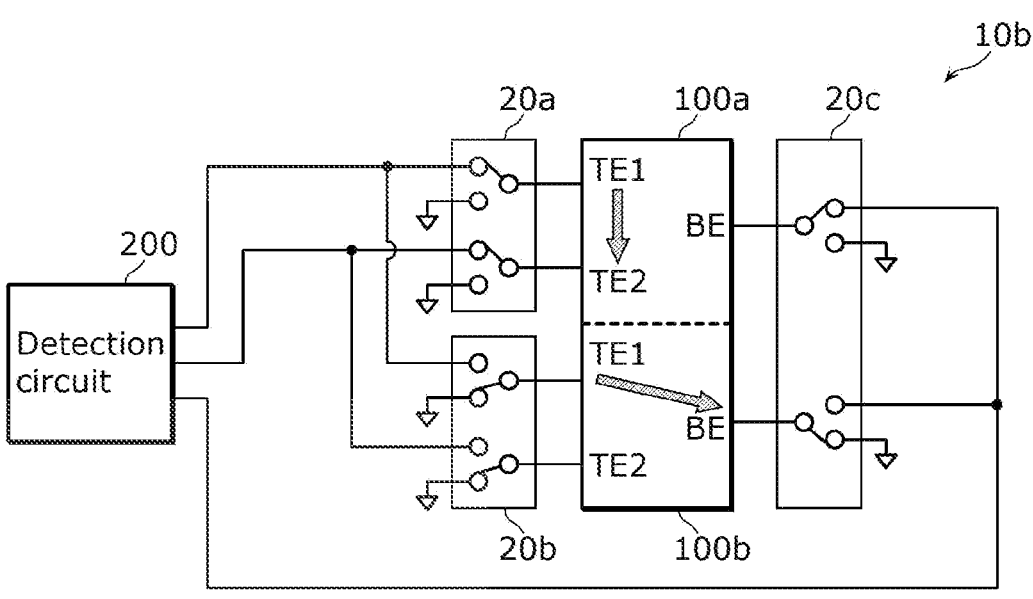
FIG. 8 is a block diagram illustrating a configuration example of a hydrogen detection device according to Variation 2 of the embodiment.

FIG. 8 is a block diagram illustrating a configuration example of hydrogen detection device 10b according to Variation 2 of the embodiment. Hydrogen detection device 10b according to the present variation includes a hydrogen sensor dedicated to the horizontal mode and a hydrogen sensor dedicated to the vertical mode. In more detail, hydrogen detection device 10b includes horizontal-mode hydrogen sensor 100a that is dedicated to the horizontal mode and vertical-mode hydrogen sensor 100b that is dedicated to the vertical mode, instead of hydrogen sensor 100 corresponding to both modes according to the embodiment. That switching circuits 20a to 20c are included is the same as in Variation 1.

Horizontal-mode hydrogen sensor 100a may be the same type of hydrogen sensor as hydrogen sensor 100 according to the embodiment, or may be a hydrogen sensor obtained by modifying the material or structure of hydrogen sensor 100 according the embodiment for an enhanced sensitivity in the horizontal mode.

Vertical-mode hydrogen sensor 100b may be the same type of hydrogen sensor as hydrogen sensor 100 according to the embodiment, or may be a hydrogen sensor obtained by modifying the material or structure of hydrogen sensor 100 according the embodiment for an enhanced sensitivity in the vertical mode.

Each of three switching circuits 20a to 20c is a switch including two single-pole, double-throw (SPDT) switches. Switching circuit 20a switches electrical continuity and discontinuity between detection circuit 200 and first and second terminals TE1 and TE2 of horizontal-mode hydrogen sensor 100a under the control of control circuit 210 included in detection circuit 200. Switching circuit 20b switches electrical continuity and discontinuity between detection circuit 200 and first and second terminals TE1 and TE2 of vertical-mode hydrogen sensor 100b under the control of control circuit 210 included in detection circuit 200. Switching circuit 20c switches electrical continuity and discontinuity between detection circuit 200 and third terminals BE of horizontal-mode hydrogen sensor 100a and vertical-mode hydrogen sensor 100b under the control of control circuit 210 included in detection circuit 200.

Operation of hydrogen detection device 10b according to the present variation (a control method for hydrogen detection device 10b) is the same as the flowchart illustrated in FIG. 5, for example. That is to say, control circuit 210 of hydrogen detection device 10b connects horizontal-mode hydrogen sensor 100a to detection circuit 200 by controlling switching circuits 20a to 20c, and detects low-concentration hydrogen in the horizontal mode using horizontal-mode hydrogen sensor 100a (S10).

Here, every time control circuit 210 obtains a hydrogen concentration converted from the resistance value, control circuit 210 determines whether the hydrogen concentration is above a threshold (e.g., the hydrogen concentration of 1%) (S11).

When the determination result is that the obtained hydrogen concentration is above the threshold (e.g., the hydrogen concentration of 1%) (Yes in S11), control circuit 210, by controlling switching circuits 20a to 20c, switches from horizontal-mode hydrogen sensor 100a to vertical-mode hydrogen sensor 100b as the hydrogen sensor connected to detection circuit 200, and detects the hydrogen concentration using vertical-mode hydrogen sensor 100b (S12).

On the other hand, when the obtained hydrogen concentration is not above the threshold (e.g., the hydrogen concentration of 1%) (No in S11), control circuit 210 continues the hydrogen detection using horizontal-mode hydrogen sensor 100a.

As described above, hydrogen detection device 10b according to Variation 2 includes: a first hydrogen sensor (horizontal-mode hydrogen sensor 100a) and a second hydrogen sensor (vertical-mode hydrogen sensor 100b) that detect hydrogen; and a first detection circuit (detection circuit 200) connected to the first hydrogen sensor (horizontal-mode hydrogen sensor 100a) and the second hydrogen sensor (vertical-mode hydrogen sensor 100b). The first hydrogen sensor (horizontal-mode hydrogen sensor 100a) includes: first electrode 103 including a principal surface and second electrode 106 including a principal surface, the principal surface of first electrode 103 and the principal surface of second electrode 106 facing each other; a first metal oxide layer (metal oxide layer 104) in contact with the principal surface of first electrode 103 and the principal surface of second electrode 106; a first insulating film (insulating films 107*a* to 107*c* etc.) covering first electrode 103, second electrode 106, and the first metal oxide layer (metal oxide layer 104); first terminal TE1 and second terminal TE2 that are connected, through via 108, to an other surface of second electrode 106 opposite the principal surface of second electrode 106; and third terminal BE connected, through via 108, to an other surface of first electrode 103 opposite the principal surface of first electrode 103. The first insulating film (insulating films 107*a* to 107*c* etc.) includes, between first terminal TE1 and second terminal TE2 in plan view of second electrode 106, a first opening (opening 106*a*) where the other surface of second electrode 106 is exposed and not covered by the first insulating film (insulating films 107*a* to 107*c* etc.). The second hydrogen sensor (vertical-mode hydrogen sensor 100*b*) includes: a third electrode (first electrode 103) including a principal surface and a fourth electrode (second electrode 106) including a principal surface, the principal surface of the third electrode (first electrode 103) and the principal surface of the fourth electrode (second electrode 106) facing each other; a second metal oxide layer (metal oxide layer 104) in contact with the principal surface of the third electrode (first electrode 103) and the principal surface of the fourth electrode (second electrode 106); a second insulating film (insulating films 107*a* to 107*c* etc.) covering the third electrode (first electrode 103), the fourth electrode (second electrode 106), and the second metal oxide layer (metal oxide layer 104); a fourth terminal and a fifth terminal (first terminal TE1 and second terminal TE2) that are connected, through via 108, to an other surface of the fourth electrode (second electrode 106) opposite the principal surface of the fourth electrode (second electrode 106); and a sixth terminal (third terminal BE) connected, through via 108, to an other surface of the third electrode (first electrode 103) opposite the principal surface of the third electrode (first electrode 103). The second insulating film (insulating films 107*a* to 107*c* etc.) includes, between the fourth terminal and the fifth terminal (first terminal TE1 and second terminal TE2) in plan view of the fourth electrode (second electrode 106), a second opening (opening 106*a*) where the other surface of the fourth electrode (second electrode 106) is exposed and not covered by the second insulating film (insulating films 107*a* to 107*c* etc.). The first detection circuit (detection circuit 200) includes a first measurement circuit (ammeters 230 and 231) that measures a first resistance value between first terminal TE1 and second terminal TE2 and a second resistance value between the sixth terminal (third terminal BE) and at least one of the fourth terminal or the fifth terminal (first terminal TE1 and second terminal TE2).

Accordingly, by selectively using hydrogen sensors 100*a* and 100*b* that are minute structures manufacturable by a semiconductor manufacturing process, low-concentration hydrogen and high-concentration hydrogen are detected. Unlike the conventional technology, this eliminates the need for a valve or the like that switches gas flow paths, thus realizing compact and wide-range hydrogen detection device 10*b* that detects low- and high-concentration hydrogen.

The first detection circuit (detection circuit 200) further includes a first control circuit (control circuit 210) that selectively outputs one of the first resistance value or the second resistance value.

The first control circuit (control circuit 210) selectively outputs the first resistance value and the second resistance value, based on the first resistance value. Accordingly, appropriate hydrogen sensor 100*a* or 100*b* is dynamically selected according to the actual hydrogen concentration, and hydrogen is detected with an appropriate measurement range.

Hydrogen detection device 10*b* also includes a first switching circuit (switching circuits 20*a* to 20*c*) that selectively connects one of the first hydrogen sensor (horizontal-mode hydrogen sensor 100*a*) or the second hydrogen sensor (vertical-mode hydrogen sensor 100*b*) to the first detection circuit (detection circuit 200). Accordingly, by selectively switching between two types of hydrogen sensors namely hydrogen sensors 100*a* and 100*b*, and connecting the switched hydrogen sensor to detection circuit 200, low-concentration hydrogen and high-concentration hydrogen are detected.

FIG. 9 is a block diagram illustrating a configuration example of hydrogen detection device 10*c* according to Variation 3 of the embodiment. Hydrogen detection device 10*c* according to the present variation includes spare hydrogen sensors in addition to the configuration of hydrogen detection device 10*b* according to Variation 2. In more detail, hydrogen detection device 10*c* includes horizontal-mode spare hydrogen sensor 110*a* that is dedicated to the horizontal mode, vertical-mode spare hydrogen sensor 110*b* that is dedicated to the vertical mode, and three switching circuits 21*a* to 21*c*, in addition to the configuration of hydrogen detection device 10*b* according to Variation 2.

Horizontal-mode spare hydrogen sensor 110*a* is a hydrogen sensor serving as a spare having the same structure as horizontal-mode hydrogen sensor 100*a*.

Vertical-mode spare hydrogen sensor 110*b* is a hydrogen sensor serving as a spare having the same structure as vertical-mode hydrogen sensor 100*b*.

Each of three switching circuits 21*a* to 21*c* is a switch including two single-pole, double-throw (SPDT) switches. Switching circuit 21*a* switches electrical continuity and discontinuity between detection circuit 200 and first and second terminals TE1 and TE2 of horizontal-mode spare hydrogen sensor 110*a* under the control of control circuit 210 included in detection circuit 200. Switching circuit 21*b* switches electrical continuity and discontinuity between detection circuit 200 and first and second terminals TE1 and TE2 of vertical-mode spare hydrogen sensor 110*b* under the control of control circuit 210 included in detection circuit 200. Switching circuit 21*c* switches electrical continuity and discontinuity between detection circuit 200 and third terminals BE of horizontal-mode spare hydrogen sensor 110*a* and vertical-mode spare hydrogen sensor 110*b* under the control of control circuit 210 included in detection circuit 200.

Although hydrogen detection device 10*c* according to Variation 3 includes two spare hydrogen sensors 110*a* and 110*b*, only one spare hydrogen sensor may be included as the spare hydrogen sensor. By selectively using one spare hydrogen sensor for the horizontal mode and the vertical mode, the one spare hydrogen sensor can function as a spare hydrogen sensor of both horizontal-mode hydrogen sensor 100*a* and vertical-mode hydrogen sensor 100*b*.

As described above, hydrogen detection device 10*c* according to Variation 3 includes: a spare hydrogen sensor (at least one of spare hydrogen sensor 110*a* or spare hydrogen sensor 110*b*) having the same structure as one of the first hydrogen sensor (horizontal-mode hydrogen sensor 100*a*) or the second hydrogen sensor (vertical-mode hydrogen sensor 100*b*); and a second switching circuit (switching circuits 21*a* to 21*c*) that selectively connects one of the first hydrogen sensor (horizontal-mode hydrogen sensor 100*a*) or the spare hydrogen sensor (at least one of spare hydrogen sensor 110*a* or spare hydrogen sensor 110*b*) to the first detection circuit, or selectively connects one of the second hydrogen sensor (vertical-mode hydrogen sensor 100*b*) or the spare hydrogen sensor (at least one of spare hydrogen sensor 110*a* or spare hydrogen sensor 110*b*) to the first detection circuit (detection circuit 200).

Accordingly, even when horizontal-mode hydrogen sensor 100*a* or vertical-mode hydrogen sensor 100*b* malfunctions, it is possible to continue the hydrogen detection using at least one of spare hydrogen sensor 110*a* or spare hydrogen sensor 110*b*, thereby improving the reliability of operation of wide-range hydrogen detection device 10*c* that detects low- and high-concentration hydrogen.

Figure 10:
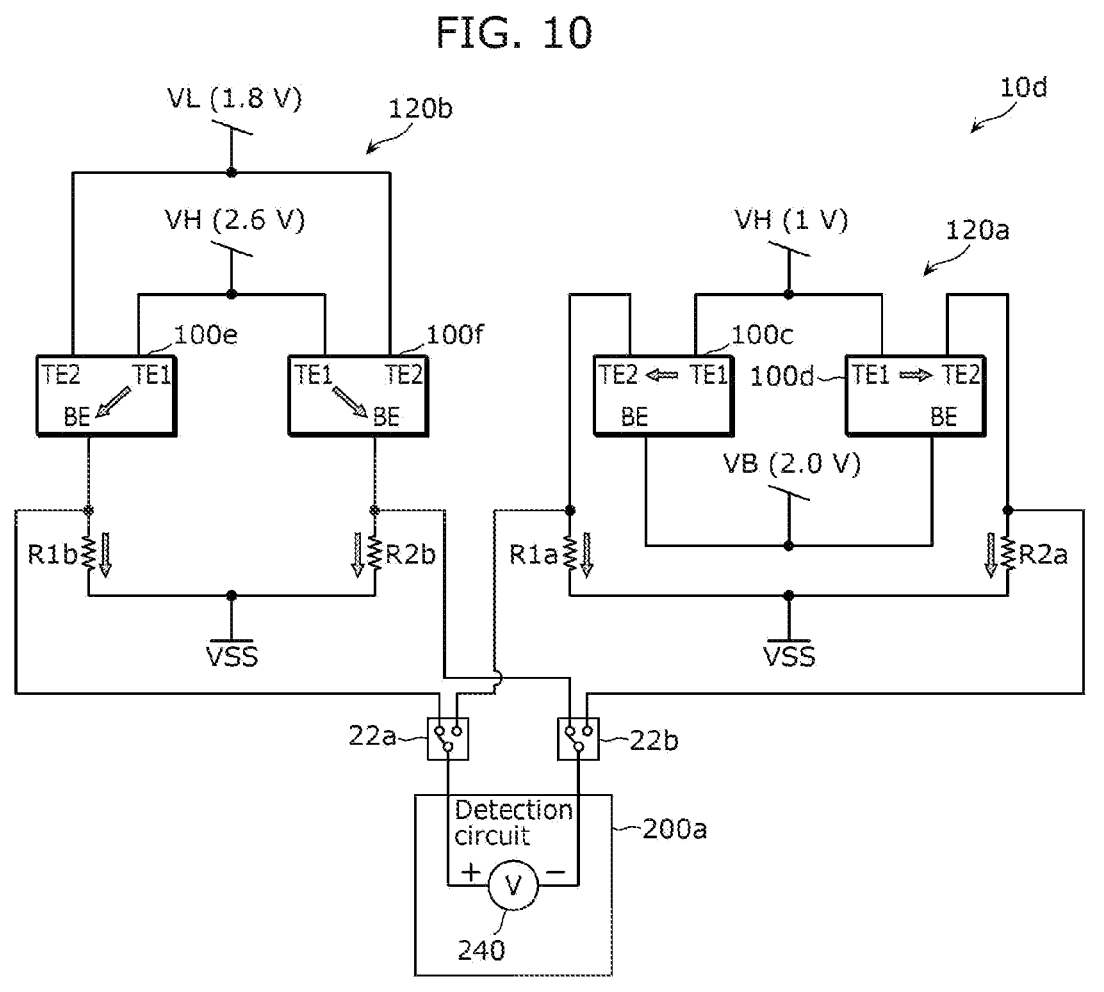

FIG. 10 is a block diagram illustrating a configuration example of hydrogen detection device 10*d* according to Variation 4 of the embodiment. Hydrogen detection device 10*d* according to the present variation includes two bridge circuits each including a hydrogen sensor. In more detail, hydrogen detection device 10*d* includes: first bridge circuit 120*a* and second bridge circuit 120*b* each including four resistive elements; two switching circuits 22*a* and 22*b*; and detection circuit 200*a* connected to first bridge circuit 120*a* and second bridge circuit 120*b* via switching circuits 22*a* and 22*b*.

Figure 11:
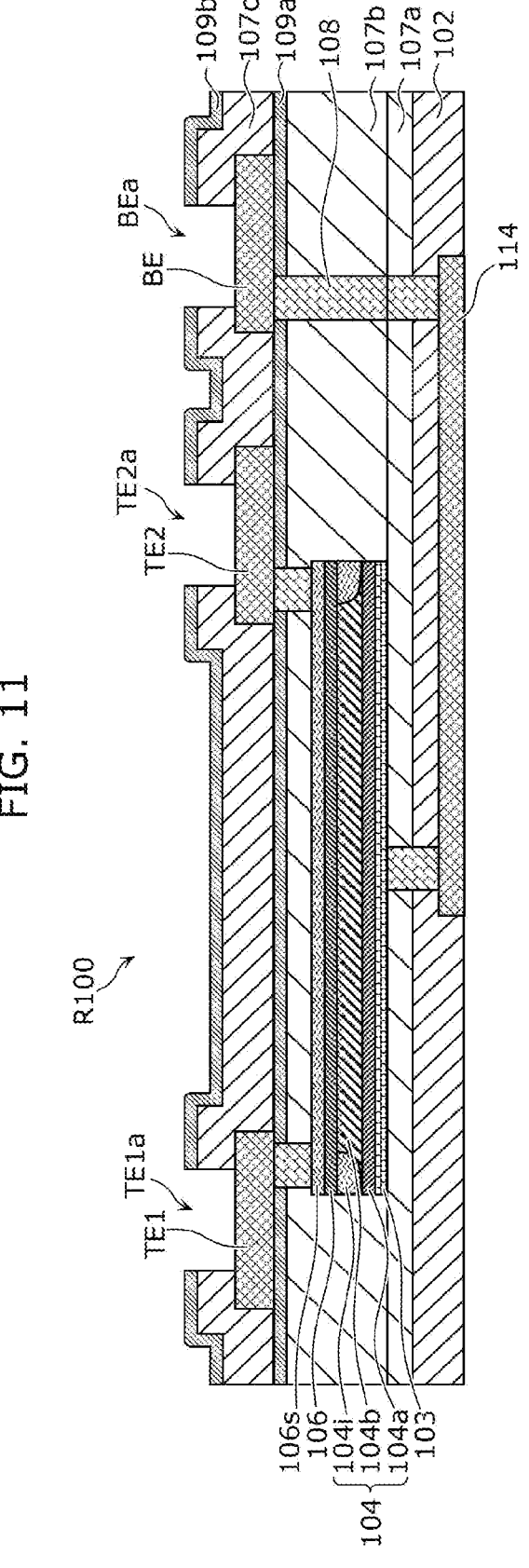
FIG. 11 is a cross-sectional view illustrating a configuration example of a resistor that has a fixed resistance value and can be applied to one of two hydrogen sensors included in a first bridge circuit in FIG. 10 and one of two hydrogen sensors included in a second bridge circuit in FIG. 10.

First bridge circuit 120*a* is a circuit for detecting low-concentration hydrogen, and includes a total of four resistive elements connected in bridge connection, namely, two resistors R1*a* and R2*a*, one horizontal-mode hydrogen sensor 100*c* that is dedicated to the horizontal mode, and resistive element 100*d* having substantially the same structure as the one hydrogen sensor. The cross-sectional structure of resistive element 100*d* having substantially the same structure as the hydrogen sensor is illustrated in FIG. 11. FIG. 11 illustrates resistor R100 that indicates a fixed resistance value, and as can be seen from figure, resistor R100 is equivalent to hydrogen sensor 100 illustrated in FIG. 1A excluding opening 106*a* (i.e., opening 106*a* is blocked). Therefore, resistor R100 is independent of the concentration of hydrogen to which resistor R100 is exposed, thereby having a fixed resistance value. Two resistors R*ia* and R2*a* are resistors that include, for example, polysilicon, and have a fixed resistance value of 20Ω, for example. As illustrated in FIG. 10, with one horizontal-mode hydrogen sensor 100*c* and resistive element 100*d*, voltage VH (1 V) is applied to first terminals TE1, voltage VB (2.0 V) is applied to third terminals BE, and second terminals TE2 are connected to reference potential (VSS) via resistors R*ia* and R2*a* so as to drive hydrogen sensor 100*c* and resistive element 100*d* in the horizontal mode.

Second bridge circuit 120*b* is a circuit for detecting high-concentration hydrogen, and includes a total of four resistive elements connected in bridge connection, namely, two resistors R1*b* and R2*b*, one vertical-mode hydrogen sensor 100*e* that is dedicated to the vertical mode, and resistive element 100*f* having substantially the same structure as the one hydrogen sensor. As with resistive element 100*d*, resistive element 100*f* has the structure illustrated in FIG. 11. Two resistors R1*b* and R2*b* are resistors that include, for example, polysilicon, and have a fixed resistance value of 10 kΩ, for example. As illustrated in FIG. 10, with one vertical-mode hydrogen sensor 100*e* and resistive element 100*f*, voltage VH (2.6 V) is applied to first terminals TE1, voltage VL (1.8 V) is applied to second terminals TE2, and third terminals BE are connected to reference potential (VSS) via resistors R1*b* and R2*b* so as to drive hydrogen sensor 100*e* and resistive element 100*f* in the vertical mode.

Detection circuit 200*a* includes voltmeter 240 for measuring a first voltage between two connection points in first bridge circuit 120*a* and a second voltage between two connection points in second bridge circuit 120*b*.

Each of switching circuits 22*a* and 22*b* is a single-pole, double-throw (SPDT) switch. Switching circuit 22*a* performs switching to selectively connect, to one of the input terminals (the positive terminal) of voltmeter 240, one of the connection point between horizontal-mode hydrogen sensor 100*c* and resistor R1*a* in first bridge circuit 120*a* or the connection point between vertical-mode hydrogen sensor 100*e* and resistor R1*b* in second bridge circuit 120*b*, under the control of detection circuit 200*a*. Switching circuit 22*b* performs switching to selectively connect, to the other of the input terminals (the negative terminal) of voltmeter 240, one of the connection point between resistive element 100*d* and resistor R2*a* in first bridge circuit 120*a* or the connection point between resistive element 100*f* and resistor R2*b* in second bridge circuit 120*b*, under the control of detection circuit 200*a*.

Accordingly, a divided voltage caused by: the hydrogen sensor or resistor R100 having substantially the same structure as the hydrogen sensor; and resistor R1*a* or R2*a* is generated at each of the two connection points between first bridge circuit 120*a* and voltmeter 240. Therefore, due to the structural similarity between the hydrogen sensor and resistor R100, the fluctuation factors of the characteristics thereof are in-phase and cancel each other out, thus ensuring operation stability against temperature fluctuations and disturbance noise. The same is true for second bridge circuit 120*b*. That is to say, a divided voltage caused by: the hydrogen sensor or resistor R100 having substantially the same structure as the hydrogen sensor; and resistor R1*b* or R2*b* is generated at each of the two connection points between second bridge circuit 120*b* and voltmeter 240. Therefore, due to the structural similarity between the hydrogen sensor and resistor R100, the fluctuation factors of the characteristics thereof are in-phase and cancel each other out, thus ensuring operation stability against temperature fluctuations and disturbance noise.

Operation of hydrogen detection device 10*d* according to the present variation (a control method for hydrogen detection device 10*d*) is the same as the flowchart illustrated in FIG. 5, for example. That is to say, first, detection circuit 200*a* connects first bridge circuit 120*a* including horizontal-mode hydrogen sensor 100*c* and resistive element 100*d* to voltmeter 240 by controlling switching circuits 22*a* and 22*b*, and detects low-concentration hydrogen in the horizontal mode using horizontal-mode hydrogen sensor 100*c* and resistive element 100*d* (S10). If their resistance balance is disrupted due to horizontal-mode hydrogen sensor 100*c* detecting hydrogen (i.e., if a difference occurs between the resistance values of hydrogen sensor 100*c* and resistive element 100*d*), voltmeter 240 measures the difference in resistance values as a polarized voltage.

Here, every time detection circuit 200*a* obtains a voltage value (or a hydrogen concentration converted from the voltage) measured by voltmeter 240, detection circuit 200*a* determines whether the voltage value (or the hydrogen concentration) is above a threshold (e.g., the hydrogen concentration of 1% or a voltage value corresponding thereto) (S11).

When the determination result is that the obtained voltage value (or the hydrogen concentration) is above the threshold (e.g., the hydrogen concentration of 1% or the voltage value corresponding thereto) (Yes in S11), detection circuit 200a, by controlling switching circuits 22a and 22b, switches from first bridge circuit 120a including horizontal-mode hydrogen sensor 100c and resistive element 100d to second bridge circuit 120b including vertical-mode hydrogen sensor 100e and resistive element 100f as the bridge circuit connected to voltmeter 240, and detects the hydrogen concentration using second bridge circuit 120b (S12).

On the other hand, when the obtained voltage value (or the hydrogen concentration) is not above the threshold (e.g., the hydrogen concentration of 1% or the voltage value corresponding thereto) (No in S11), detection circuit 200a continues the hydrogen detection using first bridge circuit 120a including horizontal-mode hydrogen sensor 100c and resistive element 100d.

As described above, hydrogen detection device 10d according to Variation 4 includes: first bridge circuit 120a and second bridge circuit 120b each including four resistive elements; and a second detection circuit (detection circuit 200a) connected to first bridge circuit 120a and second bridge circuit 120b. One of the four resistive elements included in first bridge circuit 120a is a first hydrogen sensor (horizontal-mode hydrogen sensor 100c) and one of the four resistive elements included in second bridge circuit 120b is a second hydrogen sensor (vertical-mode hydrogen sensor 100e). The second detection circuit (detection circuit 200a) includes a second measurement circuit (voltmeter 240) that measures a first voltage between two connection points in first bridge circuit 120a and a second voltage between two connection points in second bridge circuit 120b.

Accordingly, when the resistance balance between hydrogen sensors 100c, 100e and resistive elements 100d, 100f included in first bridge circuit 120a and second bridge circuit 120b is disrupted or when a difference in resistance value occurs with other resistive elements, voltmeter 240 sensitively detects that event, thus realizing wide-range hydrogen detection device 10d that detects low- and high-concentration hydrogen with high sensitivity.

Among the four resistive elements included in first bridge circuit 120a, resistive element 100d corresponding to first hydrogen sensor 100c in a positional relationship that determines the first voltage has a structure of the first hydrogen sensor excluding the first opening (opening 106a). Among the four resistive elements included in second bridge circuit 120b, resistive element 100f corresponding to second hydrogen sensor 100e in a positional relationship that determines the second voltage has a structure of the second hydrogen sensor excluding the second opening (opening 106a).

Accordingly, the four resistive elements included in first bridge circuit 120a have the same basic structure, and the resistance balance of first bridge circuit 120a can be maintained with high precision in an environment where hydrogen is not present, thus realizing highly sensitive hydrogen detection device 10d. There is also an advantage that the same manufacturing process can be applied to the four resistor elements, except for the formation of the opening. The same can be said for second bridge circuit 120b.

Figure 12:
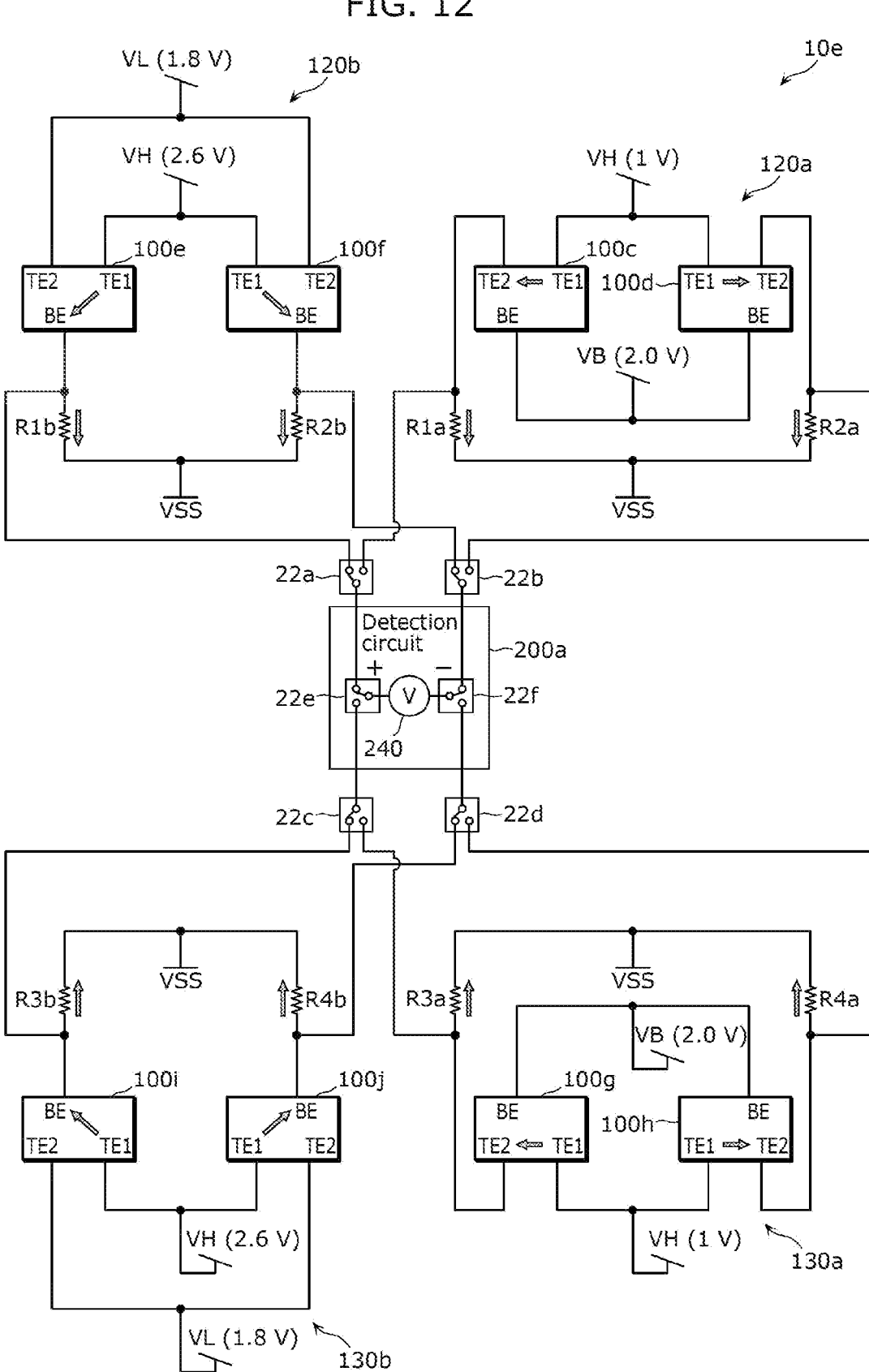
FIG. 12 is a block diagram illustrating a configuration example of a hydrogen detection device according to Variation 5 of the embodiment.

FIG. 12 is a block diagram illustrating a configuration example of hydrogen detection device 10e according to Variation 5 of the embodiment. Hydrogen detection device 10e according to the present variation includes spare bridge circuits in addition to the configuration of hydrogen detection device 10d according to Variation 4. In more detail, hydrogen detection device 10e includes two spare bridge circuits (first spare bridge circuit 130a and second spare bridge circuit 130b) and four switching circuits 22c to 22f, in addition to the configuration of hydrogen detection device 10d according to Variation 4.

First spare bridge circuit 130a has the same configuration as first bridge circuit 120a. Second spare bridge circuit 130b has the same configuration as second bridge circuit 120b. Thus, first spare bridge circuit 130a includes first hydrogen sensor 100g and resistive element 100h having substantially the same structure as the hydrogen sensor. Resistive element 100h has the structure of the first hydrogen sensor excluding the first opening (opening 106a) (i.e., resistive element 100h is resistor R100). Second spare bridge circuit 130b includes second hydrogen sensor 100i and resistive element 100j having substantially the same structure as the hydrogen sensor. Resistive element 100j has the structure of the second hydrogen sensor excluding the second opening (opening 106a) (i.e., resistive element 100j is resistor R100).

Each of switching circuits 22c and 22d is a single-pole, double-throw (SPDT) switch. Switching circuit 22c performs switching to selectively connect, to one of the input terminals of voltmeter 240, one of the connection point between horizontal-mode hydrogen sensor 100g and resistor R3a in first spare bridge circuit 130a or the connection point between vertical-mode hydrogen sensor 100i and resistor R3b in second spare bridge circuit 130b, under the control of detection circuit 200a. Switching circuit 22d performs switching to selectively connect, to the other of the input terminals of voltmeter 240, one of the connection point between resistive element 100h and resistor R4a in first spare bridge circuit 130a or the connection point between resistive element 100j and resistor R4b in second spare bridge circuit 130b, under the control of detection circuit 200a.

Each of switching circuits 22e and 22f is a single-pole, double-throw (SPDT) switch. Switching circuit 22e performs switching to selectively connect one of second bridge circuit 120b or second spare bridge circuit 130b to one of the input terminals of voltmeter 240 under the control of detection circuit 200a. Switching circuit 22f performs switching to selectively connect one of first bridge circuit 120a or first spare bridge circuit 130a to the other of the input terminals of voltmeter 240 under the control of detection circuit 200a.

An example of operation of hydrogen detection device 10e according to the present variation is the same as the processes in FIG. 7. That is to say, by controlling switching circuits 22e and 22f, in usual cases, detection circuit 200a detects low- and high-concentration hydrogen using first bridge circuit 120a and second bridge circuit 120b, and if any one of the bridge circuits is determined to be not operating normally, detection circuit 200a switches that bridge circuit to a corresponding spare bridge circuit and detects low- and high-concentration hydrogen using the spare bridge circuit.

As described above, hydrogen detection device 10e according to Variation 5 includes, in addition to the configuration of hydrogen detection device 10d according to Variation 4: a spare bridge circuit having the same configuration as one of first bridge circuit 120a or second bridge circuit 120b (in the variation, first spare bridge circuit 130a having the same configuration as first bridge circuit 120a and second spare bridge circuit 130b having the same configuration as second bridge circuit 120b); and a third switching circuit (switching circuits 22e and 22f) that selectively connects one of first bridge circuit 120a or first spare bridge circuit 130a to the second detection circuit (detection circuit 200a), or selectively connects one of second bridge circuit 120*b* or second spare bridge circuit 130*b* to the second detection circuit (detection circuit 200*a*).

Accordingly, even when one of first bridge circuit 120*a* or second bridge circuit 120*b* malfunctions, it is possible to continue the hydrogen detection using at least one of first spare bridge circuit 130*a* or second spare bridge circuit 130*b*, thereby improving the reliability of operation of wide-range hydrogen detection device 10*e* that detects low- and high-concentration hydrogen.

Although hydrogen detection device 10*e* according to Variation 5 includes two spare bridge circuits (first spare bridge circuit 130*a* and second spare bridge circuit 130*b*), only one spare bridge circuit may be included as the spare bridge circuit. Even when only one spare bridge circuit is included, the reliability of operation of the hydrogen detection device is improved as a result of the one spare bridge circuit functioning as a spare bridge circuit of corresponding first bridge circuit 120*a* or second bridge circuit 120*b*.

Figure 13A:
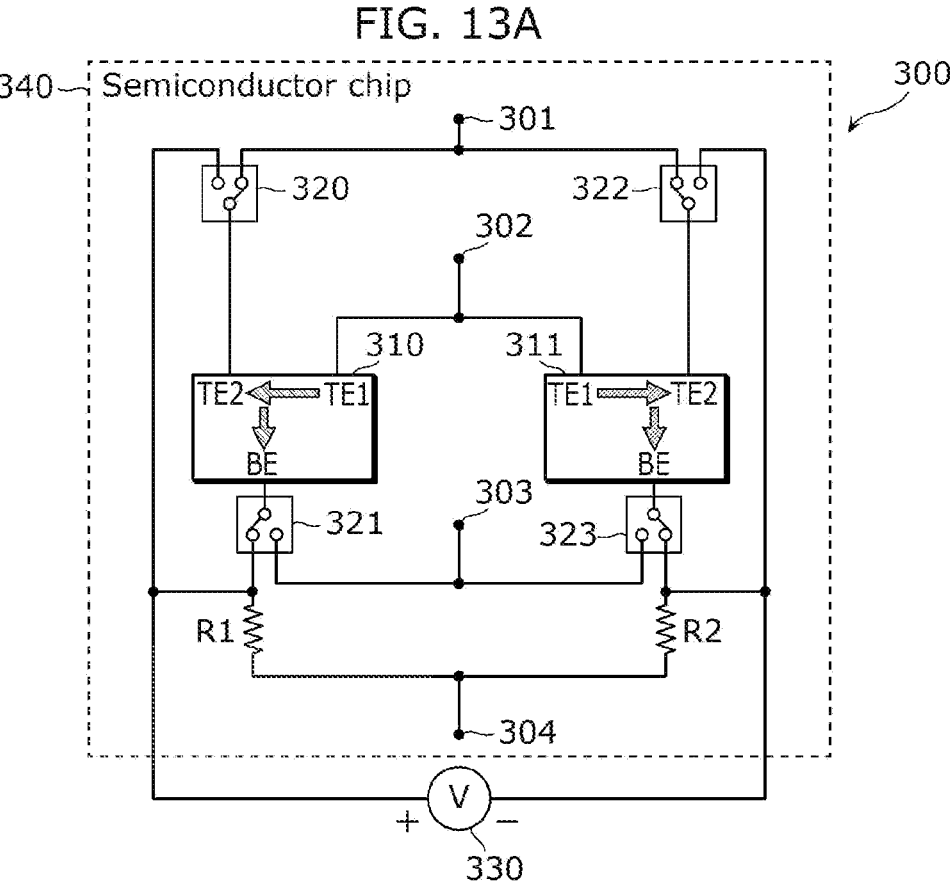
FIG. 13A is a block diagram illustrating a configuration example of a hydrogen detection device according to Variation 6 of the embodiment.

FIG. 13A is a block diagram illustrating a configuration example of hydrogen detection device 300 according to Variation 6 of the embodiment. Hydrogen detection device 300 includes semiconductor chip 340 and voltmeter 330. Formed on semiconductor chip 340 are terminals 301 to 304 connected to fixed potentials, hydrogen sensor 310 that is an example of a first resistive element included in a bridge circuit, resistor R1 that is an example of a second resistive element included in the bridge circuit, reference element 311 that is an example of a third resistive element included in the bridge circuit, resistor R2 that is an example of a fourth resistive element included in the bridge circuit, and switching circuits 320 to 323. Hydrogen detection device 300 does not necessarily require voltmeter 330.

Hydrogen sensor 310 is a sensor having the same structure as hydrogen sensor 100 illustrated in FIG. 1A and includes: first electrode 103 including a principal surface and second electrode 106 including a principal surface, the principal surface of first electrode 103 and the principal surface of second electrode 106 facing each other; a first metal oxide layer (metal oxide layer 104) in contact with the principal surface of first electrode 103 and the principal surface of second electrode 106; and a first insulating film (insulating films 107*a* to 107*c* etc.) covering first electrode 103, second electrode 106, and the first metal oxide layer (metal oxide layer 104). The first insulating film includes an opening (opening 106*a*) where the other surface of second electrode 106 opposite the principal surface of second electrode 106 is exposed and not covered by the first insulating film. Hydrogen sensor 310 further includes first terminal TE1, second terminal TE2, and third terminal BE.

Reference element 311 has the same structure as resistor R100 illustrated in FIG. 11, and is equivalent to hydrogen sensor 100 illustrated in FIG. 1A excluding opening 106*a* (i.e., opening 106*a* is blocked). That is to say, reference element 311 includes: a third electrode (first electrode 103 in FIG. 11) including a principal surface and a fourth electrode (second electrode 106 in FIG. 11) including a principal surface, the principal surface of the third electrode (first electrode 103 in FIG. 11) and the principal surface of the fourth electrode (second electrode 106 in FIG. 11) facing each other; a second metal oxide layer (metal oxide layer 104 in FIG. 11) in contact with the principal surface of the third electrode (first electrode 103 in FIG. 11) and the principal surface of the fourth electrode (second electrode 106 in FIG. 11); and a second insulating film (insulating films 107*a* to 107*c* etc. in FIG. 11) covering the third electrode (first electrode 103 in FIG. 11), the fourth electrode (second electrode 106 in FIG. 11), and the second metal oxide layer (metal oxide layer 104 in FIG. 11). The second insulating film does not include an opening where the other surface of the fourth electrode (second electrode 106 in FIG. 11) opposite the principal surface of the fourth electrode is exposed and not covered by the second insulating film. As with hydrogen sensor 310, reference element 311 further includes first terminal TE1, second terminal TE2, and third terminal BE.

Two resistors R1 and R2 are resistors that have the same resistance value, include, for example, polysilicon, and have a fixed resistance value of 20Ω, for example.

Switching circuits 320 and 321 are switches for switching hydrogen sensor 310 to one of a connection state for the horizontal mode or a connection state for the vertical mode. Specifically, to switch hydrogen sensor 310 to the connection state for the horizontal mode, switching circuit 320 connects second terminal TE2 of hydrogen sensor 310 to resistor R1, and switching circuit 321 connects third terminal BE of hydrogen sensor 310 to terminal 303, based on a control signal provided from an external source. On the other hand, to switch hydrogen sensor 310 to the connection state for the vertical mode, switching circuit 320 connects second terminal TE2 of hydrogen sensor 310 to terminal 301, and switching circuit 321 connects third terminal BE of hydrogen sensor 310 to resistor R1, based on a control signal provided from the external source.

Switching circuits 322 and 323 are switches for switching reference element 311 to one of a connection state for the horizontal mode or a connection state for the vertical mode. Specifically, to switch reference element 311 to the connection state for the horizontal mode, switching circuit 322 connects second terminal TE2 of reference element 311 to resistor R2, and switching circuit 323 connects third terminal BE of reference element 311 to terminal 303, based on a control signal provided from the external source. On the other hand, to switch reference element 311 to the connection state for the vertical mode, switching circuit 322 connects second terminal TE2 of reference element 311 to terminal 301, and switching circuit 323 connects third terminal BE of reference element 311 to resistor R2, based on a control signal provided from the external source.

Figure 13B:
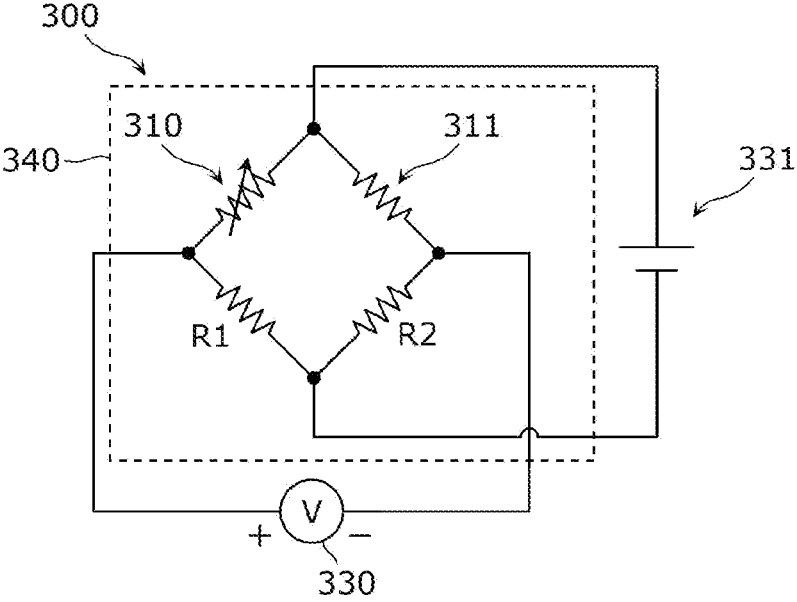
FIG. 13B is an equivalent circuit diagram of the hydrogen detection device illustrated in FIG. 13A.

FIG. 13B is an equivalent circuit diagram of hydrogen detection device 300 illustrated in FIG. 13A. For convenience of understanding, external DC voltage source 331, which is not illustrated in FIG. 13A, is illustrated here. The equivalent circuit diagram in this figure illustrates an equivalent circuit that can be applied to both of the following cases: the case where hydrogen sensor 310 and reference element 311 are in the connection state for the horizontal mode to detect low-concentration hydrogen; and the case where hydrogen sensor 310 and reference element 311 are in the connection state for the vertical mode to detect high-concentration hydrogen.

In general, when hydrogen sensor 310 is used in the horizontal mode, reference element 311 is also used in the horizontal mode, whereas when hydrogen sensor 310 is used in the vertical mode, reference element 311 is also used in the vertical mode.

As described above, hydrogen sensor 310 and reference element 311 have basically the same structure and have the same resistance value in an environment where hydrogen is not present. Resistors R1 and R2 have fixed resistance values. In an environment where hydrogen is present, only the resistance value of hydrogen sensor 310 changes, and a difference in resistance value occurs between hydrogen sensor 310 and reference element 311, resulting in a difference between the potential at the connection point of hydrogen sensor 310 and resistor R1 and the potential at the connection point of reference element 311 and resistor R2. The potential difference is measured by voltmeter 330.

As described above, hydrogen detection device 300 according to the present variation includes: a bridge circuit including a hydrogen sensor; and switching circuits 320 to 323, thus realizing a wide-range hydrogen detection device that detects low- and high-concentration hydrogen with high sensitivity.

Hydrogen sensor 310, reference element 311, and resistors R1 and R2 that are included in the bridge circuit are formed on single semiconductor chip 340 by the same semiconductor manufacturing process, thus realizing compact hydrogen detection device 300 as compared to the case of mounting these elements on a printed circuit board.

With hydrogen detection device 300 according to the present variation, hydrogen sensor 310 and reference element 311 are selectively switchable between the horizontal mode and the vertical mode; however, hydrogen sensor 310 and reference element 311 need not necessarily be switchable as such and may be fixed to either mode. Therefore, hydrogen sensor 310 and reference element 311 need not necessarily have three terminals (first terminal TE1, second terminal TE2, and third terminal BE), and may have two terminals.

With hydrogen detection device 300 according to the present variation, hydrogen sensor 310, reference element 311, and resistors R1 and R2 are formed on single semiconductor chip 340; however, only hydrogen sensor 310 and reference element 311 among these four resistive elements may be formed on single semiconductor chip 340. Both cases are no different in that hydrogen sensor 310 and reference element 311 have the same basic structure and are included in a bridge circuit, thus realizing hydrogen detection with high sensitivity.

Hereinbefore, a hydrogen detection device and a control method for a hydrogen detection device according to the present disclosure have been described based on an embodiment and variations; however, the present disclosure is not limited to the embodiment and variations. Various modifications of the present embodiment and variations as well as other embodiments resulting from combinations of some of the constituent elements from the embodiment and variations that may be conceived by those skilled in the art are intended to be included within the scope of the present disclosure as long as these do not depart from the essence of the present disclosure.

For example, with hydrogen detection device 10 according to the embodiment, detection circuit 200 includes two ammeters 230 and 231; however, the present disclosure is not limited to this configuration, and detection circuit 200 may include one ammeter and use the one ammeter by switching between the horizontal mode and the vertical mode.

With hydrogen detection device 10 according to the embodiment, detection circuit 200 includes a function to operate based on instruction CMD1 provided from an external source; however, instruction CMD1 from an external source is not necessarily essential. As illustrated in the flowchart in FIG. 5, hydrogen detection device 10 may operate in a fixed processing flow, for example constantly operating in the horizontal mode and switching to the vertical mode when the hydrogen concentration exceeds the threshold.

With hydrogen detection device 10 according to the embodiment, current flows from first terminal TE1 to second terminal TE2 in the horizontal mode; however, the direction of current flow may be reversed.

Hydrogen detection device 10 according to the embodiment is constantly driven in the horizontal mode; however, the present disclosure is not limited to such driving, and hydrogen detection device 10 may be driven to switch between the horizontal mode and the vertical mode in a time-division manner.

With hydrogen detection device 10a etc. according to Variation 1, switching circuits 20a to 20c are double-throw switches that connect a terminal of the hydrogen sensor to one of detection circuit 200 or ground; however, switching circuits 20a to 20c may simply be (on/off type) single-throw switches that connect or do not connect a terminal of the hydrogen sensor to detection circuit 200.

With hydrogen detection device 10d according to Variation 4, detection circuit 200a includes one voltmeter 240 that is selectively connected to one of first bridge circuit 120a or second bridge circuit 120b; however, the present disclosure is not limited to this configuration, and detection circuit 200a may include a total of two voltmeters, one connected to first bridge circuit 120a and the other connected to second bridge circuit 120b.

Hydrogen detection device 10e according to Variation 5 includes two spare bridge circuits (first spare bridge circuit 130a and second spare bridge circuit 130b), but instead of or in addition to these, hydrogen detection device 10e may include at least one spare hydrogen sensor replacing horizontal-mode hydrogen sensor 100c and resistive element 100d that are included in first bridge circuit 120a, or may include at least one spare hydrogen sensor replacing vertical-mode hydrogen sensor 100e and resistive element 100f that are included in second bridge circuit 120b, as in Variation 1 and Variation 3.

Although only an exemplary embodiment of the present disclosure has been described in detail above, those skilled in the art will readily appreciate that many modifications are possible in the exemplary embodiment without materially departing from the novel teachings and advantages of the present disclosure. Accordingly, all such modifications are intended to be included within the scope of the present disclosure.

INDUSTRIAL APPLICABILITY

The hydrogen detection device according to the present disclosure can be used as a wide-range hydrogen detection device that detects low- and high-concentration hydrogen, and can be used especially as a compact and wide-range hydrogen detection device that detects low- and high-concentration hydrogen, for example as a hydrogen detection device provided in a fuel-cell vehicle.

The invention claimed is:

1. A hydrogen detection device comprising:
   a first hydrogen sensor and a second hydrogen sensor that detect hydrogen; and
   a first detection circuit connected to the first hydrogen sensor and the second hydrogen sensor,
   wherein the first hydrogen sensor includes:
      a first electrode including a principal surface and a second electrode including a principal surface, the principal surface of the first electrode and the principal surface of the second electrode facing each other;
      a first metal oxide layer in contact with the principal surface of the first electrode and the principal surface of the second electrode;

a first insulating film covering the first electrode, the second electrode, and the first metal oxide layer;

a first terminal and a second terminal that are connected, through a via, to another surface of the second electrode opposite the principal surface of the second electrode; and a third terminal connected, through a via, to another surface of the first electrode opposite the principal surface of the first electrode, the first insulating film includes, between the first terminal and the second terminal in plan view of the second electrode, a first opening where the other surface of the second electrode is exposed and not covered by the first insulating film, the second hydrogen sensor includes:

a third electrode including a principal surface and a fourth electrode including a principal surface, the principal surface of the third electrode and the principal surface of the fourth electrode facing each other;

a second metal oxide layer in contact with the principal surface of the third electrode and the principal surface of the fourth electrode;

a second insulating film covering the third electrode, the fourth electrode, and the second metal oxide layer;

a fourth terminal and a fifth terminal that are connected, through a via, to another surface of the fourth electrode opposite the principal surface of the fourth electrode; and a sixth terminal connected, through a via, to another surface of the third electrode opposite the principal surface of the third electrode, the second insulating film includes, between the fourth terminal and the fifth terminal in plan view of the fourth electrode, a second opening where the other surface of the fourth electrode is exposed and not covered by the second insulating film, and the first detection circuit includes:

a first measurement circuit that measures a first resistance value between the first terminal and the second terminal and a second resistance value between the sixth terminal and at least one of the fourth terminal or the fifth terminal.

2. The hydrogen detection device according to claim 1, wherein the first detection circuit further includes:

a first control circuit that selectively outputs one of the first resistance value or the second resistance value.

3. The hydrogen detection device according to claim 2, wherein the first control circuit selectively outputs the first resistance value and the second resistance value, based on the first resistance value.

4. The hydrogen detection device according to claim 1, further comprising:

a first switching circuit that selectively connects one of the first hydrogen sensor or the second hydrogen sensor to the first detection circuit.

5. The hydrogen detection device according to claim 1, further comprising:

a spare hydrogen sensor having a same structure as one of the first hydrogen sensor or the second hydrogen sensor; and a second switching circuit that selectively connects one of the first hydrogen sensor or the spare hydrogen sensor to the first detection circuit, or selectively connects one of the second hydrogen sensor or the spare hydrogen sensor to the first detection circuit.

6. A hydrogen detection device comprising:

a first bridge circuit and a second bridge circuit each including four resistive elements; and a second detection circuit connected to the first bridge circuit and the second bridge circuit, wherein one of the four resistive elements included in the first bridge circuit is the first hydrogen sensor according to claim 1, one of the four resistive elements included in the second bridge circuit is the second hydrogen sensor according to claim 1, and the second detection circuit includes:

a second measurement circuit that measures a first voltage between two connection points in the first bridge circuit and a second voltage between two connection points in the second bridge circuit.

7. The hydrogen detection device according to claim 6, wherein among the four resistive elements included in the first bridge circuit, a resistive element corresponding to the first hydrogen sensor in a positional relationship that determines the first voltage has a structure of the first hydrogen sensor excluding the first opening, and among the four resistive elements included in the second bridge circuit, a resistive element corresponding to the second hydrogen sensor in a positional relationship that determines the second voltage has a structure of the second hydrogen sensor excluding the second opening.

8. The hydrogen detection device according to claim 6, further comprising:

a spare bridge circuit having a same configuration as one of the first bridge circuit or the second bridge circuit; and a third switching circuit that selectively connects one of the first bridge circuit or the spare bridge circuit to the second detection circuit, or selectively connects one of the second bridge circuit or the spare bridge circuit to the second detection circuit.

9. The hydrogen detection device according to claim 1, wherein the first hydrogen sensor detects hydrogen lower in concentration than hydrogen detected by the second hydrogen sensor.

10. The hydrogen detection device according to claim 1, wherein the first metal oxide layer and the second metal oxide layer each include a transition metal oxide.

11. A hydrogen detection device comprising:

a first hydrogen sensor that detects hydrogen; and a third detection circuit connected to the first hydrogen sensor, wherein the first hydrogen sensor includes:

a first electrode including a principal surface and a second electrode including a principal surface, the principal surface of the first electrode and the principal surface of the second electrode facing each other;

a first metal oxide layer in contact with the principal surface of the first electrode and the principal surface of the second electrode;

a first insulating film covering the first electrode, the second electrode, and the first metal oxide layer;

a first terminal and a second terminal that are connected, through a via, to another surface of the second electrode opposite the principal surface of the second electrode; and a third terminal connected, through a via, to another surface of the first electrode opposite the principal surface of the first electrode, the first insulating film includes, between the first terminal and the second terminal in plan view of the second electrode, a first opening where the other surface of the second electrode is exposed and not covered by the first insulating film, and the third detection circuit includes:

a third measurement circuit that measures a first resistance value between the first terminal and the second terminal and a second resistance value between the third terminal and at least one of the first terminal or the second terminal; and a second control circuit that selectively outputs one of the first resistance value or the second resistance value.

12. The hydrogen detection device according to claim 11, wherein the second control circuit selectively outputs one of the first resistance value or the second resistance value, based on the first resistance value.

13. The hydrogen detection device according to claim 11, further comprising:

a spare hydrogen sensor having a same structure as the first hydrogen sensor; and a third switching circuit that selectively connects one of the first hydrogen sensor or the spare hydrogen sensor to the third detection circuit.

14. The hydrogen detection device according to claim 11, wherein the first resistance value is more dependent on low-concentration hydrogen than the second resistance value is.

15. A hydrogen detection device comprising:

a first resistive element, a second resistive element, a third resistive element, and a fourth resistive element that are included in a bridge circuit, wherein one end of the first resistive element and one end of the second resistive element are connected, one end of the third resistive element and one end of the fourth resistive element are connected, another end of the first resistive element and another end of the third resistive element are connected, another end of the second resistive element and another end of the fourth resistive element are connected, the first resistive element is a hydrogen sensor and includes:

a first electrode including a principal surface and a second electrode including a principal surface, the principal surface of the first electrode and the principal surface of the second electrode facing each other;

a first metal oxide layer in contact with the principal surface of the first electrode and the principal surface of the second electrode; and a first insulating film covering the first electrode, the second electrode, and the first metal oxide layer, the first insulating film includes an opening where an other surface of the second electrode opposite the principal surface of the second electrode is exposed and not covered by the first insulating film, the third resistive element is a reference element and includes:

a third electrode including a principal surface and a fourth electrode including a principal surface, the principal surface of the third electrode and the principal surface of the fourth electrode facing each other;

a second metal oxide layer in contact with the principal surface of the third electrode and the principal surface of the fourth electrode; and a second insulating film covering the third electrode, the fourth electrode, and the second metal oxide layer, and the second insulating film does not include an opening where another surface of the fourth electrode opposite the principal surface of the fourth electrode is exposed and not covered by the second insulating film.

16. The hydrogen detection device according to claim 15, wherein the first resistive element includes, as the one end and the other end of the first resistive element, a first terminal and a second terminal that are connected, through a via, to the other surface of the second electrode, and the opening is located between the first terminal and the second terminal in plan view of the second electrode.

17. The hydrogen detection device according to claim 15, wherein the first resistive element includes, as the one end and the other end of the first resistive element, a terminal connected, through a via, to the other surface of the second electrode and a third terminal connected, through a via, to another surface of the first electrode opposite the principal surface of the first electrode.

18. The hydrogen detection device according to claim 15, wherein among the first resistive element, the second resistive element, the third resistive element, and the fourth resistive element, at least the first resistive element and the third resistive element are provided on a single semiconductor chip.

19. The hydrogen detection device according to claim 18, wherein the first resistive element, the second resistive element, the third resistive element, and the fourth resistive element are provided on the single semiconductor chip.

20. A control method for the hydrogen detection device according to claim 1, the control method comprising the following performed by the first detection circuit:

obtaining the first resistance value; and selectively outputting one of the first resistance value or the second resistance value, based on the first resistance value obtained.

* * * * *